(12) United States Patent
Palmer et al.

(10) Patent No.: US 8,352,195 B2
(45) Date of Patent: Jan. 8, 2013

(54) METHODS AND SYSTEMS FOR IDENTIFYING PCR PRIMERS SPECIFIC TO ONE OR MORE TARGET GENOMES

(75) Inventors: Lance E. Palmer, Plainsboro, NJ (US); Daniel Fasulo, Madison, CT (US); Lujia Chen, Princeton Junction, NJ (US); Gayle M. Wittenberg, Plainsboro, NJ (US)

(73) Assignee: Siemens Corporation, Iselin, NJ (US)

( * ) Notice: Subject to any disclaimer, the term of this patent is extended or adjusted under 35 U.S.C. 154(b) by 214 days.

(21) Appl. No.: 12/702,669

(22) Filed: Feb. 9, 2010

(65) Prior Publication Data

US 2010/0240046 A1 Sep. 23, 2010

Related U.S. Application Data

(60) Provisional application No. 61/161,956, filed on Mar. 20, 2009, provisional application No. 61/179,874, filed on May 20, 2009.

(51) Int. Cl.
*G01N 33/50* (2006.01)

(52) U.S. Cl. ......................................................... 702/19
(58) Field of Classification Search .................... None
See application file for complete search history.

(56) References Cited

OTHER PUBLICATIONS

Rozen et al. (Primer3 on the WWW for general users and for biologist programmers. In: Krawetz S, Misener S (eds) Bioinformatics Methods and Protocols: Methods in Molecular Biology. Humana Press, Totowa, NJ, pp. 365-386, 2000; README file for PRIMER3 v1.1.4, May 15, 2008, 20 pages, accessed at [http://superb-dca2.dl.sourceforge.net/project/primer3/pri.*
Liu et al. (BMC Bioinformatics 2007, 8:164, 14 pages).*
Chang et al. (Bioinformatics, vol. 19, No. 11, 2003, pp. 1311-1317).*

* cited by examiner

*Primary Examiner* — Jason Sims

(57) ABSTRACT

Methods and systems for identifying a primer pair for polymerase chain reaction specific to one or more target genomes. Methods and systems of the present disclosure can be used to identify primers that can distinguish between target genomes and closely related non-target genomes.

36 Claims, 2 Drawing Sheets

SEQUENCE LISTING

<160> NUMBER OF SEQ ID NOS: 9

<210> SEQ ID NO 1
<211> LENGTH: 23
<212> TYPE: DNA
<213> ORGANISM: Artificial sequence
<220> FEATURE:
<223> OTHER INFORMATION: Synthetic primer for distinction between
      strains of Staphylococcus aureus

<400> SEQUENCE: 1
attgtgtcat tcctcatagc tcc                                              23

<210> SEQ ID NO 2
<211> LENGTH: 21
<212> TYPE: DNA
<213> ORGANISM: Artificial sequence
<220> FEATURE:
<223> OTHER INFORMATION: Synthetic primer for distinction between
      strains of Staphylococcus aureus

<400> SEQUENCE: 2
ggaagtgagc gacatgttag a                                                21

<210> SEQ ID NO 3
<211> LENGTH: 33
<212> TYPE: DNA
<213> ORGANISM: Artificial sequence
<220> FEATURE:
<223> OTHER INFORMATION: Synthetic probe for distinction between strains
      of Staphylococcus aureus

<400> SEQUENCE: 3

-continued tgctatgcga taaaagagat aaacgccaaa ccc                                          33

<210> SEQ ID NO 4
<211> LENGTH: 19
<212> TYPE: DNA
<213> ORGANISM: Artificial sequence
<220> FEATURE:
<223> OTHER INFORMATION: Synthetic primer for distinction between
      strains of Staphylococcus aureus

<400> SEQUENCE: 4
caccactcac tgttccctc                                                          19

<210> SEQ ID NO 5
<211> LENGTH: 19
<212> TYPE: DNA
<213> ORGANISM: Artificial sequence
<220> FEATURE:
<223> OTHER INFORMATION: Synthetic primer for distinction between
      strains of Staphylococcus aureus

<400> SEQUENCE: 5
aagcagtcga agctgaacc                                                          19

<210> SEQ ID NO 6
<211> LENGTH: 31
<212> TYPE: DNA
<213> ORGANISM: Artificial sequence
<220> FEATURE:
<223> OTHER INFORMATION: Synthetic probe for distinction between strains
      of Staphylococcus aureus

<400> SEQUENCE: 6
aactgaaagt ggtacaattc acgcgattca c                                            31

<210> SEQ ID NO 7
<211> LENGTH: 21
<212> TYPE: DNA
<213> ORGANISM: Artificial sequence
<220> FEATURE:
<223> OTHER INFORMATION: Synthetic primer for distinction between
      strains of Staphylococcus aureus

<400> SEQUENCE: 7
acccaacgaa agaactagac a                                                       21

<210> SEQ ID NO 8
<211> LENGTH: 20
<212> TYPE: DNA
<213> ORGANISM: Artificial sequence
<220> FEATURE:
<223> OTHER INFORMATION: Synthetic primer for distinction between
      strains of Staphylococcus aureus

<400> SEQUENCE: 8
accttgtcgc cattaactca                                                         20

<210> SEQ ID NO 9
<211> LENGTH: 29
<212> TYPE: DNA
<213> ORGANISM: Artificial sequence
<220> FEATURE:
<223> OTHER INFORMATION: Synthetic probe for distinction between strains
      of Staphylococcus aureus

<400> SEQUENCE: 9
ctaactggct ctcctttttg taacggtcc                                               29

METHODS AND SYSTEMS FOR IDENTIFYING PCR PRIMERS SPECIFIC TO ONE OR MORE TARGET GENOMES

CROSS-REFERENCE TO RELATED APPLICATIONS

The present application claims priority to and benefit of U.S. provisional application Ser. No. 61/161,956, filed Mar. 20, 2009 and U.S. provisional application Ser. No. 61/179,874, filed May 20, 2009, the entire contents of which are herein incorporated by reference.

SEQUENCE LISTING

The present specification makes reference to a Sequence Listing (submitted electronically herewith as a .txt file named "SequenceListing.txt"). The .txt file was generated on Apr. 21, 2010 and is 3 kb in size. The entire contents of the Sequence Listing are herein incorporated by reference.

BACKGROUND

Many diagnostic methods rely on the ability to distinguish one set of organisms from another (e.g., pathogenic bacteria from non-pathogenic bacteria). Some such methods are based on polymerase chain reaction (PCR) assays that distinguish a particular genome or set of genomes from other genomes. Current methods for finding PCR primers specific to certain species or strains typically involve identifying genomic signatures, regions in which every k-mer in the sequence is unique to a target set of genomes but not found in genomes of other organisms.

SUMMARY OF CERTAIN EMBODIMENTS OF THE INVENTION

The present invention encompasses the recognition that signature-based methods are inadequate for finding PCR primers in some situations. For example, Insignia (Phillippy et al. (2007) "Comprehensive DNA signature discovery and validation," *PLoS Computational Biology* 3(7):886-894) is a software program that uses a signature-based method to find 18+ nucleotide k-mers within a set of target genomes that are not present in any other available sequences. Insignia combines these k-mers to form genomic signatures. Nevertheless, conventional implementations of this signature approach fail to find specific primers when there is no single signature common to each member in the target set of organisms or when a common signature exists but does not yield viable PCR primers. These problems typically become more pronounced as the number of target and related genomes increase.

In various aspects, the present invention provides methods and systems for identifying one or more pairs of PCR primers that distinguish a target set of genomes from a non-target set of genomes. In some embodiments, the non-target set of genomes comprises genomes related to the target set. For example, methods and systems of the invention may be used to find primers that distinguish pathogenic from non-pathogenic bacteria of the same species.

BRIEF DESCRIPTION OF THE DRAWINGS

The foregoing and other objects, aspects, features, and advantages of the disclosure will become more apparent and better understood by referring to the following description taken in conjunction with the accompanying drawings.

DEFINITIONS

Figure 1:
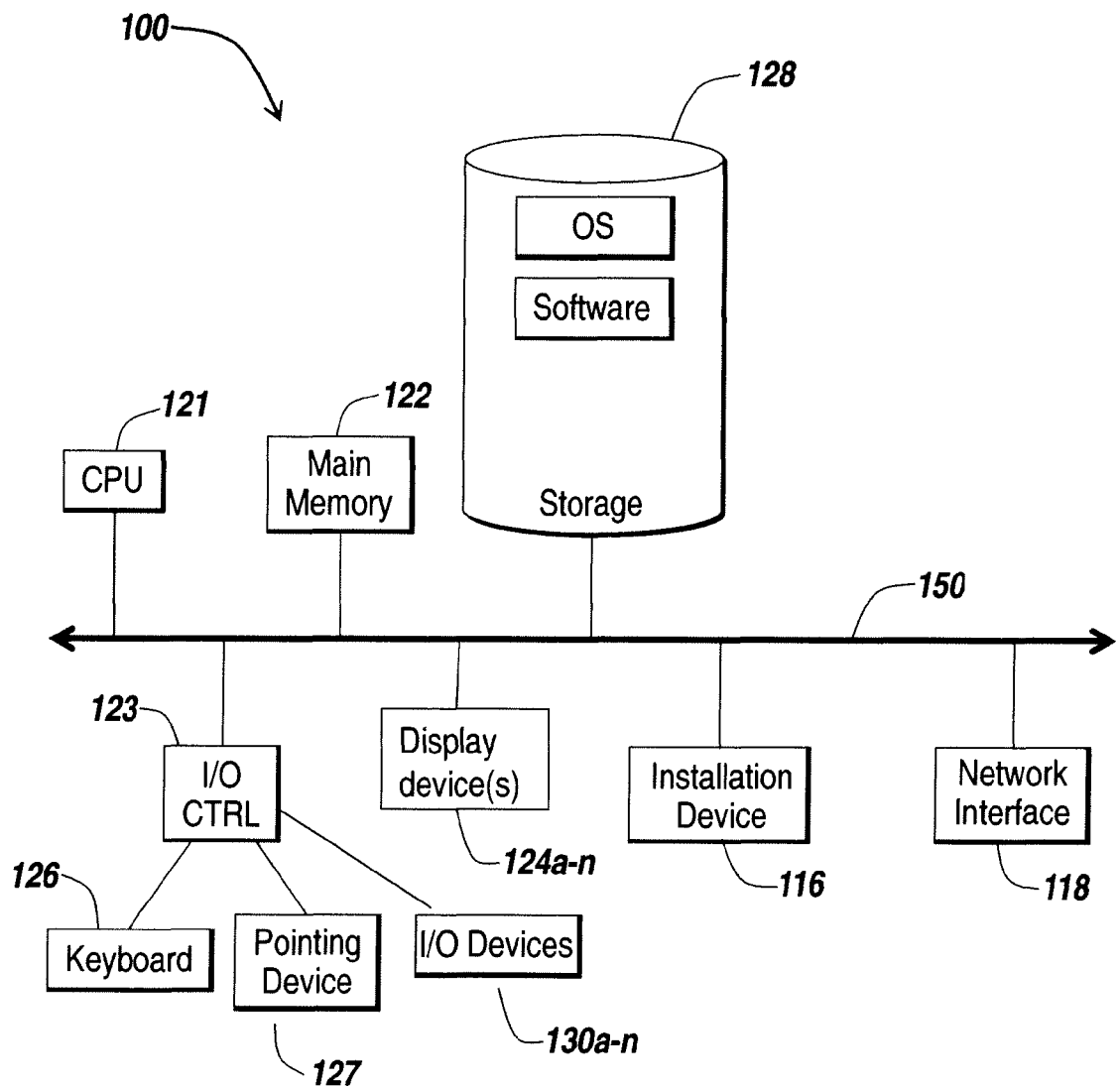
FIG. 1 is a block diagram depicting an embodiment of a computing device useful in connection with the methods and systems described herein.

As used herein, the term "alignment," when used in reference to a nucleotide or amino acid sequence, refers to the act or the result of arranging the primary sequences of a polynucleotide, or polypeptide to identify regions of similarity. In some embodiments, the regions of similarity are consequences of functional, structural, or evolutionary relationships between the sequences. Aligned sequences of nucleotide or amino acid residues are typically represented as rows within a matrix. Gaps are typically inserted between the residues so that residues with identical or similar characters are aligned in successive columns.

As used herein, the term "downstream," when used to describe relative positions of sequences (such as that of k-mers), refers to the 3' direction within a nucleic acid. Thus, a sequence that is "downstream" of another sequence can be found somewhere 3' to the other sequence. In some embodiments, the relative positions of sequences are determined in relation to their positions within a genome. In some embodiments, the downstream position corresponds to the direction of transcription (or translation) of a gene.

As used herein, the term "k-mer" refers to an oligonucleotide of length k. In some embodiments, k-mers range between a predetermined lower and upper limit, inclusive, in size. In some embodiments, the lower limit is 15, 16, 17, 18, 19, 20, 21, 22, 23, 24, or 25 nucleotides in length. In some embodiments, the upper limit is 20, 21, 22, 23, 24, 25, 26, 27, 28, 29, or 30 nucleotides in length. In some embodiments, k-mers range in size between 18 and 28 nucleotides in length, inclusive. In certain embodiments, k-mers are deoxyribonucleotides. In certain embodiments, k-mers are ribonucleotides. Predetermination of the range of k-mer length may take into account such factors as computation feasibility, length of computation time, desirability for use in particular assays (e.g., as primers for PCR, as probes for TAQMAN™), etc. In embodiments in which both primer pairs and probes are identified, the range in k-mer size may be predetermined to be the same or different.

As used herein, the term "genome" refers to the genetic information that is unique to any specific organism. In some embodiments, the term "genome" refers to the total genetic information present in the organism (i.e., a total genome). In some embodiments, the term "genome" refers to the genetic information in one complete haploid set of chromosomes of an organism, in the one or more chromosomes of a bacterium, or in the DNA or RNA of a virus. In some embodiments, the term "genome" refers to a portion of the total genetic information present in the organism (e.g., when only a partial genome is used out of choice or when only a partial genome has been sequenced or is publicly available). The phrase "target genome" refers to a genome for which primer pairs for polymerase chain reaction and/or oligonucleotide probes are identified, in that the identified primer pairs are expected to amplify a product from one or more target genomes and the identified oligonucleotide probes are expected to be able to bind to and recognize a nucleic acid from the one or more target genomes. A set of one or more target genomes may be referred to as the "target set." The phrase "non-target genome" refers to a genome that identified primer pairs and/or probe are designed to not recognize, i.e., identified primer pairs and probes can distinguish one or more target genomes from one or more non-target genomes. A set of one or more non-target genomes may be referred to as the "non-target set." The term "background set" may be used interchangeably with "non-target set."

As used herein, the term "match," when used in reference to two polynucleotides (including oligonucleotides), refers to the ability for the two polynucleotides to align together to form a heteroduplex. Where the two polynucleotides align, they typically have complementary nucleotide sequences. In some embodiments, an oligonucleotide is said to "match" another polynucleotide (e.g., a genome) if its entire sequence aligns perfectly (e.g., with no nucleotide mismatches and no gaps) over at least a portion of the other polynucleotide. In some embodiments, up to a certain number of mismatches are allowed, so long as the oligonucleotide and the other polynucleotide would be expected to hybridize stably under relevant conditions, e.g., conditions for performing a polymerase chain reaction. In some such embodiments, up to one, two, three, or four mismatches are allowed. In some embodiments, whether mismatches are allowed, and if so, how many mismatches are allowed, depends on the stringency of hybridization conditions.

As used herein, the term "melting temperature," often denoted as "$T_m$," when used to described a property of a nucleic acid, refers to the temperature at which 50% of the nucleic acid forms a stable double helix with its perfect complement and the other 50% exists as a single strand molecule. $T_m$ can be an indication of duplex stability and base composition.

As used herein, the term "probe" when used in reference to a probe for a nucleic acid, refers to a nucleic acid molecule of known sequence, which has its origin in a defined region of the genome and can be a short DNA sequence (or oligonucleotide), a PCR product, or mRNA isolate. Probes have gene-specific DNA sequences to which nucleic acids from a sample (e.g., DNA amplicons in a real-time PCR reaction) can hybridize. Probes specifically bind (or specifically hybridize) to nucleic acid of complementary or substantially complementary sequence through one or more types of chemical bonds, usually through hydrogen bond formation. In some embodiments, the probe is labeled. In some embodiments, the label on the probe is detectable when the probe is bound to the nucleic acid (e.g., PCR product) which the probe is designed to detect.

As used herein, the term "upstream," when used to described relative positions of sequences (such as that of k-mers), refers to the 5' direction within a nucleic acid. Thus, a sequence that is "upstream" of another sequence can be found somewhere 5' to the other sequence. In some embodiments, the relative positions of sequences are determined in relation to their positions within a genome. In some embodiments, the upstream position corresponds to the direction from which the polymerase (or ribosome) has come as it transcribes or translates the nucleic acid.

DETAILED DESCRIPTION OF CERTAIN EMBODIMENTS OF THE INVENTION

I. Genomes

In certain embodiments, methods and systems of the invention identify PCR primers that can be used in PCR assays to distinguish one or more target genomes within a "target set" from one or more non-target genomes within a "non-target set." Typically, methods and systems of the invention are used to identify PCR primers specific for one or more target genomes in the target set, but not specific for any non-target genomes in the non-target set. For example, primers identified by methods and systems of the present invention may be used to selectively amplify a product from one or more target genomes, but not from any non-target genomes, in a polymerase chain reaction. In some embodiments, one or more members of the target set, the non-target set, or both, are total genomes. In some embodiments, one or more members of the target set, the non-target set, or both, are partial genomes. For example, in some instances, not all of the genomic information for an organism may be used (out of choice or because it has yet be sequenced and/or become publicly available). Methods of the invention may nevertheless be employed to identify PCR primers distinguishing total genomes and/or partial genomes from a target set from total genomes and/or partial genomes from a non-target set.

In some embodiments, methods and systems of the invention identify oligonucleotide probes that may be used in any of a variety of molecular biological assays, for example in kinetic PCR assays and other real-time PCR assays (e.g., TAQMAN™).

In some embodiments, the target genomes and non-target genomes (whether total or partial) range from about 1 kb (kilobases) to about 10 Mb (megabases) in size. In some embodiments, the genomes range from about 1 kb to 5 about kb, from about 5 kb to about 10 kb, from about 10 kb to about 15 kb, or from about 15 kb to 20 kb in size. In some embodiments, the genomes range from about 20 kb to about 30 kb, about 30 kb to about 40 kb, or about 40 kb to about 50 kb in size. In some embodiments, the genomes range from about 50 kb to 1 Mb in size. In some embodiments, the genomes range from about 1 Mb to about 3 Mb in size. In some embodiments, the genomes range from about 3 Mb to about 5 Mb in size. In some embodiments, the genomes range from about 5 Mb to 7 Mb in size. In some embodiments, the genomes range from about 7 Mb to about 10 Mb in size.

In some embodiments, the non-target set comprises at least one genome that is related to at least one genome in the target set. For example, in some embodiments, the organism of at least one non-target genome is of the same genus as the organism of at least one target genome. In some such embodiments, the organism of at least one non-target genome is of the same species as the organism of at least one target genome.

In some embodiments, the organisms of all the genomes in the non-target set are of the same genus as the organism of at least one target genome. In some such embodiments, the organism of all the genomes in the non-target set is of the same species as the organism of at least one target genome.

Additionally or alternatively, in some embodiments, the non-target set comprises at least one genome whose sequences show similarities with at least one target genome. In some embodiments, the non-target set comprises at least one genome having up to about 99.8%, 99.7%, 99.6%, 99.5%. 99.4%, 99.3%, 99.2%, 99.1%, 99.0%, 98.9%, 98.8%, 98.7%. 98.6%. 98.5%. 98.4%, 98.3%, 98.2%, 98.1%, 98.0%, 97.9%, 97.8%, 97.7%, 97.6%, 97.5%, 97.4%, 97.3%, 97.2%, 97.1%, 97.0%, 96.9%, 96.8%, 96.7%, 96.6%, 96.5%, 96.4%, 96.3%, 96.2%, 96.1%, 96.0%, 95.9%, 95.8%, 95.7%, 95.6%, 95.5%, 95.4%, 95.3%, 95.2%, 95.1%, or 95.0% overall sequence identity with at least one target genome. In some embodiments, the non-target set comprises at least one genome having up to about 94.5%, 94.0%, 93.5%, 93.0%, 92.5%, 92.0%, 91.5%, 91.0%, 90.5%, or 90.0% overall sequence identity with at least one target genome. In some embodiments, the non-target set comprises at least one genome having up to about 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, or 65% overall sequence identity with at least one target genome.

In some embodiments, all genomes in the non-target set have up to about 99.8%, 99.7%, 99.6%, 99.5%. 99.4%, 99.3%, 99.2%, 99.1%, 99.0%, 98.9%, 98.8%, 98.7%. 98.6%. 98.5%. 98.4%, 98.3%, 98.2%, 98.1%, 98.0%, 97.9%, 97.8%, 97.7%, 97.6%, 97.5%, 97.4%, 97.3%, 97.2%, 97.1%, 97.0%, 96.9%, 96.8%, 96.7%, 96.6%, 96.5%, 96.4%, 96.3%, 96.2%, 96.1%, 96.0%, 95.9%, 95.8%, 95.7%, 95.6%, 95.5%, 95.4%, 95.3%, 95.2%, 95.1%, or 95.0% overall sequence identity with at least one target genome. In some embodiments, all genomes in the non-target set have up to about 94.5%, 94.0%, 93.5%, 93.0%, 92.5%, 92.0%, 91.5%, 91.0%, 90.5%, or 90.0% overall sequence identity with at least one target genome. In some embodiments, all genomes in the non-target set have up to about 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, or 65% overall sequence identity with at least one target genome.

In some embodiments, the organism of at least one genome in the target set, non-target set, or both, is a microorganism. Non-limiting examples of types of microorganisms for which methods and systems of the present invention may identify specific primers and/or probes include viruses, bacteria, and fungi.

In some embodiments, primers and/or probes identified by methods and systems of the invention can be used to distinguish between closely related species or between strains of a particular species. For example, primers and/or probes may be used to distinguish between pathogenic and non-pathogenic microorganisms, between microorganisms resistant to antibiotics and those sensitive to antibiotics, between strains or substrains of microorganisms for which certain vaccines have varying degrees of effectiveness, etc. For example, the target set could comprise genomes of pathogenic microorganisms and the non-target set could comprise genomes of non-pathogenic microorganisms, or vice versa.

II. Methods

In one aspect, provided are methods for identifying at least one pair of primers for PCR that can be used to distinguish one or more target genomes in a target set from one or more target genomes in a non-target set.

Methods disclosed herein generally comprise steps that lead to the identification of an initial plurality of k-mers based on one or more genomes of the target set. The methods generally further comprise steps resulting in identification of potential primer pairs from the initial plurality of k-mers.

In some embodiments, methods disclosed herein comprise steps of: (a) storing an identification of an initial plurality of k-mers in a target set, wherein each k-mer in the initial plurality of k-mers is an oligonucleotide within a particular size range and is identified from one or more genomes in the target set; (b) determining for each genome in a non-target set, if and optionally where each k-mer in the initial plurality of k-mers matches the genome in the non-target set; (c) storing for at least one k-mer in the initial plurality of k-mers, an identification that it matches a genome in the non-target set, optionally with a location at which it matches the genome; (d) identifying a first k-mer in the initial plurality of k-mers that does not match any of the genomes in the non-target set; (e) identifying a second k-mer in the initial plurality of k-mers located within a specified number of bases of the identified first k-mer in a target genome; (f) identifying the first k-mer and the second k-mer as a primer pair for use in a polymerase chain reaction; and (g) storing an identification of the primer pair.

In some of these embodiments, the methods comprise steps of: (a) storing, by a k-mer selection component executing on a computing device comprising a processor and a storage element, in a data structure, an identification of an initial plurality of k-mers in the target set, the data structure stored by the storage element of the computing device, wherein each k-mer in the initial plurality of k-mers is an oligonucleotide within a particular size range and is identified from one or more genomes in the target set; (b) determining, by a k-mer mapping component executing on the computing device, for each genome in a non-target set, if and optionally where each k-mer in the initial plurality of k-mers matches the genome in the non-target set; (c) storing, by the k-mer mapping component, in the data structure, for at least one k-mer in the initial plurality of k-mers, an identification that it matches a genome in the non-target set, optionally with a location at which it matches the genome; (d) identifying, by a k-mer finding component executing on the computing device, a first k-mer in the initial plurality of k-mers that does not match any of the genomes in the non-target set; (e) identifying, by a k-mer locator component executing on the computing device, a second k-mer in the initial plurality of k-mers located within a specified number of bases of the identified first k-mer in a target genome; (f) identifying, by a k-mer analysis component executing on the computing device, the first k-mer and the second k-mer as a primer pair for use in a polymerase chain reaction; and (g) storing, by the k-mer analysis component, an identification of the primer pair on the storage element of the computing device.

In other embodiments, methods disclosed herein comprise steps of: (a) storing an identification of an initial plurality of k-mers in the target set, wherein each k-mer in the initial plurality of k-mers is an oligonucleotide within a particular size range and is identified from one or more genomes in the target set; (b) identifying for a first k-mer in the initial plurality of k-mers, a second k-mer in the initial plurality located within a specified number of bases downstream of the first k-mer; (c) determining that the first k-mer and second k-mer do not recognize any genome from the non-target set, wherein the first k-mer and second k-mer are not considered to recognize a given genome if: (i) at least one of the k-mers does not match the given genome, or (ii) the first and second k-mer match the given genome but not within the specified number of bases; (d) identifying the first k-mer and the second k-mer as a primer pair for use in a polymerase chain reaction; and (e) storing an identification of the primer pair on the storage element of the computing device.

In some of these embodiments, the methods comprise steps of: (a) storing, by a k-mer selection component executing on a computing device comprising a processor and a storage element, in a data structure, an identification of an initial plurality of k-mers in the target set, the data structure stored by the storage element of the computing device, wherein each k-mer in the initial plurality of k-mers is an oligonucleotide within a particular size range and is identified from one or more genomes in the target set; (b) identifying, by a k-mer locator component executing on the computing device, for a first k-mer in the initial plurality of k-mers, a second k-mer in the initial plurality located within a specified number of bases downstream of the first k-mer; (c) determining, by a k-mer mapping component executing on the computing device, that the first k-mer and second k-mer do not recognize any genome from the non-target set, wherein the first k-mer and second k-mer are not considered to recognize a given genome if: (i) at least one of the k-mers does not match the given genome, or (ii) the first and second k-mer match the given genome but not within the specified number of bases; (d) identifying, by a k-mer analysis component executing on the computing device, the first k-mer and the second k-mer as a primer pair for use in a polymerase chain reaction; and (e) storing, by the k-mer analysis component, an identification of the primer pair on the storage element of the computing device.

A. Storing in a Data Structure Identification of an Initial Plurality of k-mers in a Target Set In some embodiments, the initial plurality of k-mers in a target set can be stored using a k-mer selection component executing on a computing device (as described herein) in a data structure. In some embodiments, the k-mer selection component accesses genomic sequence information for each genome in the target set. Genomic sequence information may be available on a storage device on the computing device, and/or on a database on a storage element on another computing device to which the computing device is connected (for example, via a network). For example, genomic sequence information is available in a variety of public databases, including, but not limited to, the Entrez PubMed at National Center for Biotechnology Information (NCBI) (available at the website whose address is "http" followed immediately by "://www.ncbi.nlm.nih.gov") and the European Molecular Biology Laboratory—European Bioinformatics Institute's genomes pages (available at the website whose address is "http" followed immediately by "://www.ebi.ac.uk/genomes/"). In some embodiments, genomic sequence information is stored in a file accessible by the k-mer selection component. The genomic sequence information can be stored in a variety of formats, including FASTA (a.k.a Pearson) format.

In some embodiments, the k-mer selection component parses the genomic sequence systematically such that all, or a threshold number of, possible k-mers having a length of a predetermined range are read by the k-mer selection component. For example, the genome sequence may be read starting at position 1, and the sequence from position one through the kth position (wherein k is the length of the k-mer) is read and stored at least temporarily for further manipulations and/or analysis. Then the genome sequence may be read starting at position 2, and the sequence from position one through the (k+1) position is read and subject to further manipulations and/or analysis and/or stored (e.g., as a string) at least temporarily to be accessed later. In addition to sequence information of each k-mer, information such as an identification of the target genome from which the k-mer is read, location within the target genome (using either or both ends of the k-mer), and or strand of the k-mer (e.g., sense or anti-sense, plus or minus) may be obtained and/or stored.

Thus, for example, in embodiments in which k-mers are predetermined to be of a length between 18 and 28 nucleotides inclusive, one way of parsing a target genome to generate an initial plurality of k-mers would begin with starting at position 1 and then reading the sequence of nucleotides from position 1 to position 18 as a k-mer, then reading nucleotides from position 1 to position 19 as a k-mer, then reading nucleotides from position 1 to position 20 as a k-mer, and so on and so forth until nucleotides from position 1 to position 28 have been read as a k-mer. Then the k-mer selection component would begin at position 2 in the target genome and read nucleotides from position 2 to position 19 as a k-mer, then read positions 2 through positions 20 as a k-mer, and so on, and so forth, until nucleotides from position 2 to position 29 have been read as a k-mer. This process can continue until a particular condition has been met, for example, until the entire target genome has been read, until a sufficient number of k-mers has been read, and/or until a sufficient number of k-mers passing one or more filters (as discussed below) has been read. In some embodiments, this process can be repeated for each target genome in a target set.

It will be understood by one of ordinary skill in the art that the target genome need not be read for k-mers in the particular order described above, and that the target genomes within a set may be read sequentially in any order and/or read in parallel.

In certain embodiments, one or more filters are applied to k-mers read from a target genome. In some embodiments, the one or more filters are applied immediately after the k-mer is read and before storing information about such k-mers to a data structure. In some embodiments, storing information for the k-mer to a data structure is contingent on the k-mer having passed the one or more filters. Storing information only for k-mers that pass the one or more filters may allow reduction in computation time. Filters that may be applied to k-mers include filters for desirable characteristics of PCR primers.

In some embodiments, a filter for guanine-cytosine (GC) content is applied to each k-mer, and k-mers within a particular range are deemed to pass the filter and those outside the range are not allowed to pass. In some embodiments, k-mers having a GC content ranging from 20% to 80% (inclusive) are allowed to pass the filter. In some embodiments, k-mers having a GC content ranging from 30% to 80% (inclusive) are allowed to pass the filter. In some embodiments, k-mers having a GC content ranging from 40% to 60% (inclusive) are allowed to pass the filter. (A GC content of 20% means that 20% of the bases in the k-mer are either guanine or cytosine.)

In some embodiments, a filter for melting temperature ($T_m$) is applied to each k-mer, and k-mers within a particular range of $T_m$ are deemed to pass the filter. In some embodiments, k-mers having a $T_m$ ranging between 50° C.-65° C. inclusive are allowed to pass the filter. In some embodiments, the lower limit for the range of acceptable $T_m$ is about 50° C., 51° C., 52° C., 53° C., 54° C., or 55° C., wherein the range is inclusive of the lower limit. In some embodiments, the upper limit for the range of acceptable $T_m$ is about 53° C., 54° C., 55° C., 56° C., 57° C., 58° C., 59° C., 60° C., 61° C., 62° C., 63° C., 64° C., or 65° C. wherein the range is inclusive of the upper limit. A variety of formulas for predicting $T_m$ for a given k-mer are known in the art. (See, e.g., Panjkovich (2005) "Comparison of different melting temperature calculation methods for short DNA sequences." *Bioinformatics*, 21(6): 711-722; Sambrook et al. (1989) "Molecular Cloning: A Laboratory Manual," Cold Spring Harbor Press, Cold Spring Harbor, N.Y.; Mueller et al. (1993) in "Current Protocols in Molecular Biology 15.5," Greene Publishing Associates, Inc. and John Wiley and Sons, New York; SantaLucia (1998) "A unified view of polymer, dumbbell, and oligonucleotide DNA nearest-neighbor thermodynamics," *Proc Natl Acad Sci USA*. 95(4):1460-5; von Ahsen et al. (1999) "Application of a thermodynamic nearest-neighbor model to estimate nucleic acid stability and optimize probe design: prediction of melting points of multiple mutations of apolipoprotein B-3500 and factor V with a hybridization probe genotyping assay on the LightCycler," *Clinical Chemistry*, 45:2094-2101; and Nakano et al. (1999) "Nucleic acid duplex stability: influence of base composition on cation effects," *Nucleic Acids Research*, 27: 2957-2965, the entire contents of each of which are herein incorporated by reference.)

In certain embodiments, $T_m$ is calculated using an algorithm or module. Many algorithms or modules for $T_m$ calculation are available online or as part of a software package. Non-limiting examples of readily available programs that include modules for k-mer $T_m$ determination include PRIMER3 and MELTING (available from the European Molecular Biology Laboratory—European Bioinformatics Institute). See, e.g., Rozen and Skaletsky (2000) "Primer3 on the WWW for General Users and for Biologist Programmers." Methods in Molecular Biology. 132: 365-386; and the website whose address is "http" followed immediately by "://www.ebi.ac.uk/compneur-srv/melting/", the entire contents of each of which are herein incorporated by reference in their entirety.

In some embodiments, $T_m$ in Celsius degrees is calculated according to Equation 1, also known as the Wallace rule:

$$T_m = 2(A+T) + 4(G+C) \quad \text{(Equation 1)}$$

wherein the A, G, C, and T, are the number of occurrences of each nucleotide (adenosine, guanosine, cytidine, and thymidine respectively) in the k-mer. Equation 1 was developed particularly for membrane-bound k-mers between 14 and 20 nucleotides in size, inclusive, in salt conditions of 0.9 M NaCl; however, equation 1 may be used for k-mers of other sizes and in other conditions. In some embodiments, Equation 1 is used for k-mers having less than 14 nucleotides in length.

In some embodiments, $T_m$ in Celsius is calculated according to Equation 2:

$$T_m = 64.9 + 41(G+C-16.4)/L \quad \text{(Equation 2)}$$

wherein G and C are the number of occurrences of guanosine and cytidine in the k-mer and L is the length of the primer. In some embodiments, Equation 2 is used for k-mers longer than 14 nucleotides in length.

In some embodiments, $T_m$ is calculated according to an equation that allows an adjustment for salt concentration. In some embodiments, $T_m$ is calculated according to an equation that allows an adjustment for formamide concentration.

In some embodiments, $T_m$ in Celsius is calculated according to Equation 3:

$$T_m = 81.5 + 16.6 \log M + 41(XG + XC) - \frac{500}{L} - 0.62F \quad \text{(Equation 3)}$$

wherein M is the molar concentration of monovalent cations, XG and XC are the mole fractions of guanosine and cytosine in the k-mer, L is the length of the shortest string in the duplex, and F is the molar concentration of formamide. Several variations of Equation 3 are used in the art, and any of such variations may be used in calculating $T_m$ for a k-mer.

In some embodiments, $T_m$ is calculated using thermodynamic basis sets for nearest neighbor interactions, thereby taking into account the sequence of the k-mer. (See, e.g., SantaLucia (1998) "A unified view of polymer, dumbbell, and oligonucleotide DNA nearest-neighbor thermodynamics," Proc Natl Acad Sci USA. 95(4):1460-5.) (Thus, k-mers having the same composition of bases but different sequences may have different calculated $T_m$ values). In some such embodiments, $T_m$ is calculated according to Equation 4:

$$T_m = \left( \frac{\Delta H \cdot 1000}{A + \Delta S + R\log(C_{k-mer}/4)} \right) - 273.15 + 16.6 \log[Na^+] \quad \text{(Equation 4)}$$

wherein $\Delta H$ is the sum of the nearest neighbor enthalpy changes for hybrids change in enthalpy; A is a small constant containing corrections for helix initiation; $\Delta S$ is the sum of the nearest-neighbor entropy changes; R is the gas constant (1.987 cal deg$^{-1}$ mol$^{-1}$); $C_{k-mer}$ is the molar concentration of the k-mer; and [Na$^+$] is the salt concentration.

In some embodiments, A is not used (i.e., A is assumed to be zero). In some embodiments, the adjustment for salt concentration (i.e., the term 16.6 log [Na$^+$]) is not used. In some embodiments, $C_{k-mer}/4$ is replaced by $C_{k-mer}$ if the k-mer is self-complementary. In some embodiments, $C_{k-mer}/4$ is replaced by $C_{k-mer}/2$.

In some embodiments, a k-mer concentration of between about 20 nM and 500 nM is used is assumed for the purpose of calculating $T_m$. In some embodiments, a k-mer concentration of about 200 nM is assumed for the purpose of calculating $T_m$. In some embodiments, a k-mer concentration of about 50 nM is assumed for the purpose of calculating $T_m$.

In some embodiments, a salt concentration of between about 10 mM and about 1.5 M is used for the purpose of calculating $T_m$. In some embodiments, a salt concentration of about 900 mM is used for the purpose of calculating $T_m$. In some embodiments, a salt concentration of about 50 mM is used for the purpose of calculating $T_m$.

In some embodiments in which a thermodynamic nearest neighbor interactions method is used to calculate $T_m$, entropy and enthalpy values for dinucleotide and nucleotide interactions are approximately as shown in Appendix C, which depicts the script for an exemplary PERL module for calculating melting temperature. In some embodiments in which a thermodynamic nearest neighbor interactions method is used to calculate $T_m$, entropy and enthalpy values for dinucleotide and nucleotide interactions are approximately as shown in Table 1:

TABLE 1

| Interaction | DNA | | RNA | |
| --- | --- | --- | --- | --- |
| | $\Delta H$ | $\Delta S$ | $\Delta H$ | $\Delta S$ |
| AA/TT | −9.1 | −24.0 | −6.6 | −18.4 |
| AT/TA | −8.6 | −23.9 | −5.7 | −15.5 |
| TA/AT | −6.0 | −16.9 | −8.1 | −22.6 |
| CA/GT | −5.8 | −12.9 | −10.5 | −27.8 |
| GT/CA | −6.5 | −17.3 | −10.2 | −26.2 |
| CT/GA | −7.8 | −20.8 | −7.6 | −19.2 |
| GA/CT | −5.6 | −13.5 | −13.3 | −35.5 |
| CG/GC | −11.9 | −27.8 | −8.0 | −19.4 |
| GC/CG | −11.1 | −26.7 | −14.2 | −34.9 |
| GG/CC | −11.0 | −26.6 | −12.2 | −29.7 |
| Initiation | 0.0 | −10.8 | 0.0 | −10.8 |

In some embodiments, PRIMER3 is used to calculate melting temperature using the above so-called SantaLucia thermodynamic parameters and salt corrections.

In some embodiments, a filter to ensure lack of consecutive runs of bases is applied to each k-mer. In such embodiments, k-mers having consecutive runs of the same base for a threshold number or greater do not pass the filter, while those that lack such consecutive runs are allowed to pass the filter. In some embodiments, the threshold number is 4. That is, k-mers that have 4 or more cytosines in a row, four or more guanines in a row, four or more thymines in a row, and/or four or more adenines in a row, are not allowed to pass the filter. In some embodiments, the threshold number is 5. In some embodiments, the threshold number is 6.

In some embodiments, a filter against self-annealing is applied to each k-mer. In such embodiments, k-mers that are predicted to self-anneal do not pass the filter, while those that are not are allowed to pass the filter.

In certain embodiments, information about k-mers from the initial plurality of k-mers is stored to a data structure.

In some embodiments, the data structure is a hash table. In some such embodiments, a string representing either the k-mer sequence or the reverse complement of the k-mer sequence is used as the hash key. In some embodiments, the k-mer sequence is compared to the reverse complement sequence and the lower value (alphabetically) is used as the hash key. In some embodiments, the k-mer sequence is compared to the reverse complement sequence and the upper value (alphabetically) is used as the hash key.

In some embodiments, additional information is stored in the data structure, for example, an identification of the target genome from which the k-mer was obtained, the position of the k-mer in the target genome, and the strand of the target genome from which the k-mer was identified (e.g., plus or minus, or sense or antisense).

In certain embodiments, the process of generating an initial plurality of k-mers from a target genome, optionally applying one or more filters, and storing information about the k-mers in a data structure is repeated for each target genome in the target set.

In some embodiments, information in the data structure is printed to a file such as a text file.

Appendix A depicts an exemplary PERL script, pickKmers.pl, that generates a list of k-mers of predetermined length from genomes (such as target genomes); applies GC content, melting temperature, and consecutive runs filters to the k-mers; and stores information (e.g., a sequence string, position, and length) about k-mers passing the filters in a hash table as described above. pickKmers.pl uses a variety of modules, including some described herein and some that are available in the art. For example, PERL modules for predicting melting temperatures and for performing sequence alignments are available at online collections such as the Bioperl distribution site (see the web address "http:" followed immediately by "//bioperl.org", the entire contents of which are herein incorporated by reference).

pickKmers.pl calls and uses information in a configuration file using a module such as multiSpi.pm, depicted in Appendix B. From a configuration file, multiSpi.pm parses parameters for minimum and maximum k-mer length, minimum and maximum melting temperature, minimum and maximum GC content, and maximum consecutive runs of a single base.

pickKmers.pl also reads genomic sequence information (e.g., of a target genome) stored in a file and systematically parses the genomic sequence to generate and save information (e.g., sequence information, identification of genome from which they were read, position, and strand) relating to an initial plurality of k-mers. In some embodiments, the genome sequence is stored in FASTA (a.k.a. Pearson) format. pickKmers.pl skips k-mers that contain undefined bases (e.g., Ns are skipped). In some embodiments, duplicate k-mers are removed.

pickKmers.pl applies filters to each k-mer. In some embodiments, pickKmers.pl ignores a k-mer if it has previously not passed a filter. To calculate melting temperature for each k-mer, pickKmers.pl uses a module such as TM.pm (depicted in Appendix C). pickKmers.pl also uses a module simpleAlign.pm (depicted in Appendix D) to generate global and local ungapped alignment scores. For k-mers that pass the melting temperature, consecutive run, and GC content filters, their information is stored to a hash table.

B. Mapping k-mers in the Initial Plurality to Non-Target Genomes

In some embodiments, a k-mer mapping component executing on the computing device can be used to "map" the k-mers in the initial plurality by performing sequence alignments. For k-mers that match a non-target genome, the position where it matches the non-target genome may be stored in the data structure. Alternatively a simple identification that it matches a non-target genome may be stored in the data structure. In certain embodiments, a predetermined number of nucleotide mismatches are allowed when aligning the k-mers to the non-target genomes. In some embodiments, up to 5, up to 4, up to 3, up to 2, or up to 1 mismatch(es) is/are allowed. In certain embodiments, no mismatches are allowed.

In some embodiments, sequences of k-mers in the initial plurality of k-mers are written to a file such as a text file and used as the input file for one or more programs that perform sequence alignments between the k-mers and genomes in the non-target set. In some embodiments, SeqMap is used. (See, e.g., Jiang and Wong (2008) "SeqMap: mapping massive amount of oligonucleotides to the genome," *Bioinformatics*, 24(20):2395-2396). In some embodiments, at least two alignment programs are used together to increase the number of matches (between k-mers and non-target genomes) found. For example, BOWTIE and SNAPPER may be used together. (See, e.g., Langmead et al. (2009) "Ultrafast and memory-efficient alignment of short DNA sequences to the human genome," *Genome Biology*, 4; 10(3):R25; and Walenz, "Informatics research k-mer tools," website address "http" followed immediately by "://kmer.sourcefourge.net", the entire contents of each of which are herein incorporated by reference). BOWTIE efficiently maps k-mers to a sequence with 0 to 3 mismatches, but cannot currently find matches with gaps. SNAPPER will find matches with gaps, as well as with a small number of mismatches, but requires one exactly matching k-mer to serve as a seed. Thus, SNAPPER does not necessarily find all matches that have mismatches.

In some embodiments, after k-mers have been mapped to non-target genomes, a new file (e.g., a text file) of the data structure is generated that includes an indication that the k-mers match a non-target genome, optionally with positions of the k-mers within non-target genomes.

Appendix E depicts an exemplary PERL script, mapKmers.seqmap.pl, that performs sequence alignments between k-mers (such as those whose information is stored in a text file generated by pickKmers.pl) and non-target genomes using BOWTIE and SNAPPER. mapKmers.seqmap.pl generates a new data structure that further includes positions of k-mers within non-target genomes.

C. Identifying Potential Primer Pairs and/or Probes

1. Identifying Pairs of Primers Unique to the Target Set

In certain embodiments, methods identify at least one pair of PCR primers wherein at least one primer in the pair is unique to (i.e., specific to) the target set in that it matches a sequence in one or more genomes in the target set, but does not match a sequence in any of the genomes in the non-target set.

All k-mers in the initial plurality of k-mers match at least one genome in the target set, as the k-mers were generated by parsing the target genomes. However, a given k-mer might only match a subset of the genomes in a target set, though there may be some k-mers in the initial plurality that match all the genomes in a target set. In some embodiments, k-mers from the initial plurality of k-mers are sorted by the number of target genomes within a target set that they match. In some such embodiments, k-mers within a data structure are examined as described below in order of number of target genomes matched, with those matching the greatest number of target genomes being examined first.

In some embodiments, a k-mer finding component executing on the computing device identifies a first k-mer in the initial plurality of k-mers that does not match any of the genomes in the non-target set. K-mers that match one or more non-target genomes are skipped.

For each first k-mer identified, a k-mer locator component executing on the computing device then identifies one or more k-mers in the initial plurality that are located within a specified number of bases (e.g., either upstream or downstream) of the identified first k-mer in the target genome. Each other k-mer within a specified number of bases can be considered a "second k-mer" to be analyzed as part of a primer pair with the first k-mer, whether or not the second k-mer is unique to the target set.

In some embodiments, the specified number of bases is defined in a configuration file. In some embodiments, the specified number of bases is 40 kb or less, 30 kb or less, 20 kb or less, 15 kb or less, 10 kb or less, 9 kb or less, 8 kb or less, 7 kb or less, 6 kb or less, 5 kb or less, 4 kb or less, 3 kb or less, or 2 kb or less. In some embodiments, the specified number of bases is 5000 bases or less. In some embodiments, the specified number of bases is 1500 bases or less, 1200 bases or less, 1000 bases or less, 800 bases or less, 600 bases or less, 500 bases or less, 400 bases or less, 350 bases or less, 300 bases or less, 250 bases or less, 200 bases or less, or 150 bases or less. In some embodiments, the specified number of bases is between 100 and 400 bases, inclusive. In some embodiments, the specified number of bases is between 100 and 300 bases, inclusive.

A k-mer analysis component executing on the computing device analyzes each pair of k-mers, identifying those that have potential as a primer pair. In some embodiments, the step of identifying those that have potential as a primer pair comprises a step of determining that the first k-mer and second k-mer do not hybridize to each other; in other words, first k-mer and second k-mers that are predicted to hybridize to each other are not considered further. In some embodiments, the k-mer analysis component uses a program such as PRIMER3 (Rozen et al. (2000)). Information about k-mer pairs that are deemed useful as potential primer pairs can be stored in an array.

In some embodiments, pairs of k-mers from each target genome are analyzed. If a pair of k-mers had already been identified in a target genome, that pair is skipped and not analyzed again. However, for each pair of first and second k-mers identified, an identification of all target genomes matched by the pair may be recorded, optionally with positions of k-mers within each target genome and strands.

In some embodiments, a k-mer locator component executing on the computing device calculates the number of genomes hit by both the first k-mer and second k-mer and then sorts the pair (first k-mer and second k-mer) by number of genomes matched by the pair.

In some embodiments, the steps of the methods are repeated for each target genome in the target set. In some embodiments, the steps are repeated for each target genome in sequence (i.e., each step is performed on target genome A, then each step is performed on target genome B, etc.). In some embodiments, each step is repeated for each target genome before the next step is initiated (i.e., the first step is repeated for target genome A, target genome B, etc. then the second step is repeated for target genome A, target genome B, etc.). It is to be understood that any and all variations in the sequence of steps is encompassed by the present methods.

In some embodiments, the k-mer analysis component also identifies oligonucleotide probes in the sequence flanked by the first k-mer and second k-mer; programs such as PRIMER3 may be used for doing so.

In some embodiments, one or more rules are employed to reduce the number of pairs analyzed by the k-mer analysis component. Adhering to such rules may reduce expenditure of computational resources. For example, a threshold number of k-mer pairs matching a certain set of genomes may be set (e.g., in a configuration file), and once the threshold has been met, no further k-mer pairs matching the particular set of genomes are analyzed.

For example, if the threshold of 10 pairs is set and 10 primer pairs matching genomes 1, 2, and 3 have been identified by the k-mer analysis component, then no additional pairs of k-mers that match genomes 1, 2, and 3 are analyzed. If 10 primer pairs matching genomes 4, 5, and 6 have also been identified by the k-mer analysis component, then no additional pairs of k-mers that match genomes 4, 5, and 6 are analyzed, but a k-mer pair matching genomes 2, 3, and 4 is analyzed. Thus, in these embodiments, the threshold number of pairs relate to a pattern of genomes matched (e.g., genomes 1, 2, and 3; genomes 4, 5, and 6; or genomes 2, 3, and 4) and not to an individual genome.

In some embodiments, a set-covering algorithm is run to find a minimal set of primer pairs that will collectively match all the genomes in a target set. See, e.g., Example 1.

Appendix F shows an exemplary PERL script, pickPairs.pl, that identifies primer pairs as described above.

2. Identifying Pairs of Primers that Combined are Unique to the Target Set

In certain embodiments, methods identify at least one pair of PCR primers, wherein the combined pair of primers is unique to (i.e., specific to) the target set.

In some embodiments, neither of the primers in the pair matches any sequence in any of the non-target genomes.

In some embodiments, one of the primers in the pair matches a sequence in at least one of the non-target genomes, but the other in the pair does not, such that the pair would not be expected to amplify a product from any of the non-target genomes in a PCR reaction.

In some embodiments, both of the primers in the pair match a sequence in at least one of the non-target genomes, but the pair of primers would not be expected to amplify a product from any of the non-target genomes in a PCR reaction. For example, each of the primers in the pair may match a sequence in at least one of the non-target genomes, but they do not both match sequences in the same non-target genome(s). Alternatively or additionally, the primers in a pair may match sequences in the same non-target genome(s), but they match sequences that are too far apart for the primers to be expected to amplify a product from a non-target genome.

In some embodiments, k-mers in the initial plurality are sorted based on position within a target genome, and each k-mer is analyzed in order of position as a "first k-mer" of a pair of k-mers to be analyzed.

For each first k-mer, a k-mer locator component executing on the computing device identifies one or more k-mers within a specified number of bases of the first k-mer and downstream to the first k-mer. Each other k-mer within a specified number of bases can be considered a "second k-mer" to be analyzed as part of a primer pair with the first k-mer.

In some embodiments, the specified number of bases is defined in a configuration file. In some embodiments, the specified number of bases is 40 kb or less, 30 kb or less, 20 kb or less, 15 kb or less, 10 kb or less, 9 kb or less, 8 kb or less, 7 kb or less, 6 kb or less, 5 kb or less, 4 kb or less, 3 kb or less, or 2 kb or less. In some embodiments, the specified number of bases is 5000 bases or less. In some embodiments, the specified number of bases is 1500 bases or less, 1200 bases or less, 1000 bases or less, 800 bases or less, 600 bases or less, 500 bases or less, 400 bases or less, 350 bases or less, 300 bases or less, 250 bases or less, 200 bases or less, or 150 bases or less.

In some embodiments, the specified number of bases is between 100 and 400 bases, inclusive. In some embodiments, the specified number of bases is between 100 and 300 bases, inclusive.

If the pair of k-mers (first k-mer and second k-mer) could be used to amplify a product from one or more genomes in the non-target set (i.e., it "recognizes" a non-target genome), it is not saved for further analysis. In some embodiments, recognizing a genome for a pair of k-mers means that the k-mers match sequences within the same genome within a predetermined distance such that the pair of k-mers would be expected to amplify a product form the genome in a polymerase chain reaction. In some embodiments, the specified number of bases is defined in a configuration file. In some embodiments, the predetermined distance is specified in a configuration file. In some embodiments, the predetermined distance is 5 kilobases (kb) or less, 4.5 kb or less, 4.0 kb or less, 3.5 kb or less, 3.0 kb or less, 2.5 kb or less, 2.0 kb or less, 1500 bases or less, 1200 bases or less, 1000 bases or less, 800 bases or less, 600 bases or less, 500 bases or less, 400 bases or less, 350 bases or less, 300 bases or less, 250 bases or less, 200 bases or less, or 150 bases or less. In some embodiments, the predetermined distance is the same as the specified number of bases used when finding second k-mers. In some embodiments, the predetermined distance is greater than the specified number of bases used when finding second k-mers.

Thus, in general, the first k-mer and second k-mer are not considered to recognize a given genome if: (i) at least one of the k-mers does not match the given genome or (ii) the first and second k-mers do not match within the predetermined distance of each other in the given genome.

A k-mer analysis component executing on the computing device analyzes each pair of k-mers, identifying those that have potential as a primer pair. In some embodiments, the step of identifying those that have potential as a primer pair comprises a step of determining that the first k-mer and second k-mer do not hybridize to each other; in other words, first k-mer and second k-mers that are predicted to hybridize to each other are not considered further. In some embodiments, the k-mer analysis component uses a program such as PRIMER3 (Rozen et al. (2000)). Information about k-mer pairs that are deemed useful as potential primer pairs can be stored in an array.

In some embodiments, pairs of k-mers from each target genome are analyzed. If a pair of k-mers had already been identified in a target genome, that pair is skipped and not analyzed again. However, for each pair of first and second k-mers identified, an identification of all target genomes matched by the pair may be recorded, optionally with positions of k-mers within each target genome and strands.

In some embodiments, a k-mer locator component executing on the computing device calculates the number of genomes hit by both the first k-mer and second k-mer and then sorts the pair (first k-mer and second k-mer) by number of genomes matched by the pair.

In some embodiments, the steps of the methods are repeated for each target genome in the target set. In some embodiments, the steps are repeated for each target genome in sequence (i.e., each step is performed on target genome A, then each step is performed on target genome B, etc.). In some embodiments, each step is repeated for each target genome before the next step is initiated (i.e., the first step is repeated for target genome A, target genome B, etc. then the second step is repeated for target genome A, target genome B, etc.). It is to be understood that any and all variations in the sequence of steps is encompassed by the present methods.

In some embodiments, the k-mer analysis component also identifies oligonucleotide probes in the sequence spanned by the first k-mer and second k-mer pair; programs such as PRIMER3 may be used for doing so.

As with the above-described methods of identifying pairs of primers each unique to the target set, in some embodiments, one or more rules are employed to reduce the number of pairs analyzed by the k-mer analysis component. For example, as described above, a threshold number of k-mer pairs matching a certain set of genomes may be set (e.g., in a configuration file), and once the threshold has been met, no further k-mer pairs matching the particular set of genomes are analyzed.

In some embodiments, a set-covering algorithm is run to find a minimal set of primer pairs that will collectively recognize all the genomes in a target set.

Appendix F shows an exemplary PERL script, pickPairs.pl, that identifies primer pairs as described above.

As understood by those of ordinary skill in the art, variations of the scripts and modules depicted herein may be used. Furthermore, a variety of scripting and programming languages can be used to encode any or any combination of the above functionalities.

The designations of components discussed herein are not intended to imply that each functionality is restricted to one component, nor are such designations intended to imply that each component provides only one functionality. For example, a single component may provide more than one functionality. Furthermore, two or more components that are given separate designations may be the same component.

III. Systems

A. Computing Environments

A variety of computing environments may be deployed in the practice of embodiments of the present invention. A computing device 100 may be deployed as and/or executed on any type and form of computing device, such as a computer, network device or appliance capable of communicating on any type and form of network and performing the operations described herein. FIG. 1 depicts a block diagram of a computing device 100 useful for practicing an embodiment of the methods and systems described herein. As shown in FIG. 1, a computing device 100 includes a central processing unit 121, and a main memory unit 122. As shown in FIG. 1, a computing device 100 may include a storage element 128, an installation device 116, a network interface 118, an I/O controller 123, display devices 124*a-n*, a keyboard 126 and a pointing device 127, such as a mouse. The storage element 128 may include, without limitation, an operating system, data and software (e.g., executable application programs).

The central processing unit 121 is any logic circuitry that responds to and processes instructions fetched from the main memory unit 122. In many embodiments, the central processing unit 121 is provided by a microprocessor unit, such as: those manufactured by Intel Corporation of Mountain View, Calif.; those manufactured by Motorola Corporation of Schaumburg, Ill.; those manufactured by Transmeta Corporation of Santa Clara, Calif.; the RS/6000 processor, those manufactured by International Business Machines of White Plains, N.Y.; or those manufactured by Advanced Micro Devices of Sunnyvale, Calif. The computing device 100 may be based on any of these processors, or any other processor capable of operating as described herein. The main memory unit 122 may be one or more memory chips capable of storing data and allowing any storage location to be directly accessed by the microprocessor 121.

A wide variety of I/O devices 130*a*-130*n* may be present in the computing device 100. Input devices include keyboards, mice, trackpads, trackballs, microphones, and drawing tablets. Output devices include video displays, speakers, inkjet printers, laser printers, and dye-sublimation printers. The I/O devices may be controlled by an I/O controller 123 as shown in FIG. 1. The I/O controller may control one or more I/O devices such as a keyboard 126 and a pointing device 127, e.g., a mouse or optical pen. Furthermore, an I/O device may also provide storage and/or an installation medium 116 for the computing device 100. In some embodiments, the computing device 100 may provide USB connections (not shown) to receive handheld USB storage devices such as the USB Flash Drive line of devices manufactured by Twintech Industry, Inc. of Los Alamitos, Calif.

Referring still to FIG. 1, the computing device 100 may support any suitable installation device 116, such as a floppy disk drive for receiving floppy disks such as 3.5-inch, 5.25-inch disks or ZIP disks, a CD-ROM drive, a CD-R/RW drive, a DVD-ROM drive, tape drives of various formats, USB device, hard-drive or any other device suitable for installing software and programs. The computing device 100 may further comprise a storage device, such as one or more hard disk drives or redundant arrays of independent disks, for storing an operating system and other related software, and for storing application software programs such as any program related to the client agent 120. Optionally, any of the installation devices 116 could also be used as the storage device.

In certain embodiments, a computing device 100a is connected via at least one network to another computer 100b. In some such embodiments, the network is a local-area network (LAN), such as a company Intranet, a metropolitan area network (MAN), or a wide area network (WAN) (such as the Internet or the World Wide Web). In some embodiments, the computing device 100 may include a network interface 118 to interface to a network through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, CDMA, GSM, WiMax and direct asynchronous connections). The network interface 118 may comprise a built-in network adapter, network interface card, PCMCIA network card, card bus network adapter, wireless network adapter, USB network adapter, modem or any other device suitable for interfacing the computing device 100 to any type of network capable of communication and performing the operations described herein.

In some embodiments, the computing device 100 comprises or is connected to multiple display devices 124a-124n, which each may be of the same or different type and/or form. As such, any of the I/O devices 130a-130n and/or the I/O controller 123 may comprise any type and/or form of suitable hardware, software, or combination of hardware and software to support, enable, or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In some embodiments, a video adapter comprises multiple connectors to interface to multiple display devices 124a-124n. In some embodiments, the computing device 100 includes multiple video adapters, with each video adapter connected to one or more of the display devices 124a-124n. In some embodiments, any portion of the operating system of the computing device 100 is configured for using multiple displays 124a-124n. In some embodiments, one or more of the display devices 124a-124n is/are provided by one or more other computing devices, such as computing devices 100a and 100b connected to the computing device 100, for example, via a network. These embodiments may include any type of software designed and constructed to use another computer's display device as a second display device 124a for the computing device 100. One ordinarily skilled in the art will recognize and appreciate the various ways and embodiments that a computing device 100 may be configured to have multiple display devices 124a-124n.

In some embodiments, an I/O device 130 is a bridge between the system bus 150 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a SerialPlus bus, a SCI/LAMP bus, a Fibre-Channel bus, or a Serial Attached small computer system interface bus.

A computing device 100 of the sort depicted in FIG. 1 typically operates under the control of operating systems, which control scheduling of tasks and access to system resources. The computing device 100 can run any operating system such as any of the versions of the MICROSOFT WINDOWS operating systems, any of the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 3.x, WINDOWS 95, WINDOWS 98, WINDOWS 2000, WINDOWS NT 3.51, WINDOWS NT 4.0, WINDOWS 2003, WINDOWS 2008. WINDOWS CE, WINDOWS XP, and WINDOWS VISTA, all of which are manufactured by Microsoft Corporation of Redmond, Wash.; MAC OS, manufactured by Apple Inc., of Cupertino, Calif.; OS/2, manufactured by International Business Machines of Armonk, N.Y.; and Linux, a freely-available operating system distributed by Caldera Corp. of Salt Lake City, Utah, or any type and/or form of a Unix operating system.

The computing device 100 can be any workstation, desktop computer, laptop or notebook computer, server, handheld computer, mobile telephone or other portable telecommunication device, media playing device, gaming system, mobile computing device, or other type and/or form of computing, telecommunications or media device that is capable of communication and that has sufficient processor power and memory capacity to perform the operations described herein. In some embodiments, the computing device 100 comprises different processors, operating systems, and input devices consistent with the device. In someembodiments, the computing device 100 comprises a combination of devices, such as a mobile phone combined with a digital audio player or portable media player.

B. Systems for Identifying Pairs of PCR Primers

Figure 2:
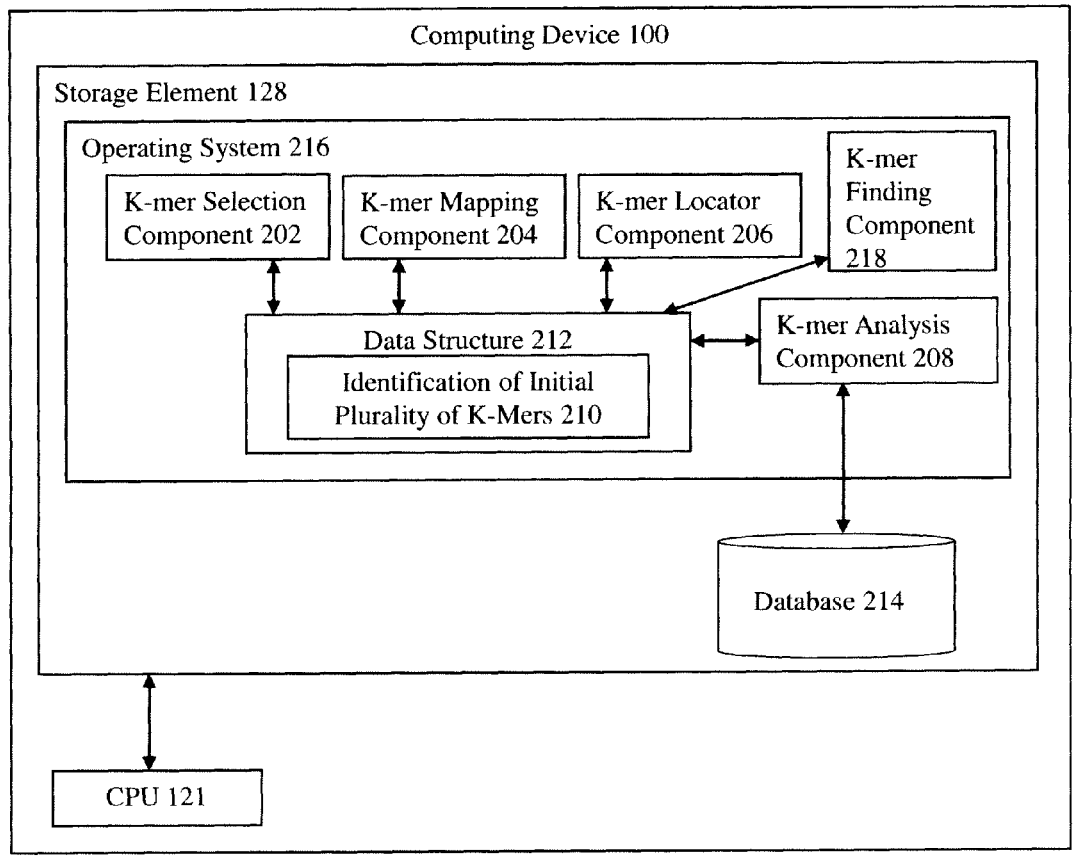
FIG. 2 is a block diagram depicting one embodiment of a system for identifying a pair of primers for polymerase chain reaction specific to one or more target genomes within a target set but not to any non-target genomes within a non-target set.

Referring now to FIG. 2, a block diagram depicts one embodiment of a system for identifying a pair of PCR primers that distinguish one or more target genomes from one or more non-target genomes. In brief overview, the system includes a k-mer selection component 202, a k-mer mapping component 204, an optional k-mer finding component 218, a k-mer locator component 206, and a k-mer analysis component 208. Each component executes on a computing device 100 comprising a processor 121 and a storage element 128 (that comprises an operating system 216). In certain embodiments the computing device 100 comprises one or more databases 214 (e.g., genomic databases) that are in communication with the k-mer analysis component 208. In some embodiments, the computing device 100 is a computing device as described above in connection with FIG. 1.

In general, the k-mer selection component 202 stores, in a data structure 212, an identification of an initial plurality of k-mers 210 from one or more target genomes within the target set, wherein a k-mer identified in the initial plurality of k-mers is an oligonucleotide within a particular range of size as described above. The data structure 212 may be stored by the storage element 128 of the computing device 100.

1. Systems for Identifying Pairs of Primers Unique to the Target Set

In some embodiments the system is designed to identify pairs of primers that are unique to the target set. According to such embodiments, the k-mer mapping component 204 determines if, and optionally where, each k-mer in the initial plurality matches a genome in the non-target set. In some embodiments, the k-mer mapping component 204 stores, in the data structure, for at least one k-mer in the initial plurality of k-mers, an identification that matches a genome in the non-target set, optionally with a location at which it matches the genome.

In such embodiments, the k-mer finding component 218 is present and identifies a first k-mer in the initial plurality of k-mers 210 that does not match any of the genomes in the non-target set.

The k-mer locator component 206 identifies a second k-mer in the initial plurality of k-mers 210 located within a specified number of bases of the identified first k-mer in a target genome.

Finally, the k-mer analysis component 208 identifies the first k-mer and the second k-mer as a primer pair for use in a polymerase chain reaction. In some embodiments, the k-mer analysis component 208 stores an identification of the primer pair on the storage element 128 of the computing device 100.

2. Systems for Identifying Pairs of Primers that Combined are Unique to the Target Set In some embodiments the system is designed to identify pairs of primers that combined are unique to the target set. According to such embodiments, the k-mer finding component 218 is absent (or not used) and the k-mer locator component 206 identifies, for a first k-mer in the initial plurality of k-mers, a second k-mer in the initial plurality located within a specified number of bases downstream of the first k-mer.

The k-mer mapping component 204 then determines that the first k-mer and second k-mer do not recognize any genome from the non-target set, wherein the first k-mer and second k-mer are not considered to recognize a given genome if: (i) at least one of the k-mers does not match the given genome, or (ii) the first and second k-mer match the given genome but not within the specified number of bases.

Finally, the k-mer analysis component 208 identifies the first k-mer and the second k-mer as a primer pair for use in a polymerase chain reaction. In some embodiments, the k-mer analysis component 208 stores an identification of the primer pair on the storage element 128 of the computing device 100.

3. Other System Features

In some embodiments, the k-mer selection component 202 stores the data structure 212 in a storage element such as buffer, a cache, a data store, a flat file, or any other format. It will be appreciated that the storage element may be implemented in RAM, flash memory, a hard disk, or any other storage medium. In some embodiments, the data structure 212 is stored on the computing device 100 (e.g., in the storage element 128). In other embodiments, the data structure 212 resides on a second computing device, accessible over a network.

In some embodiments, the k-mer selection component 202 includes a data structure generation component for generating the data structure 212. In another embodiment, the k-mer selection component 202 is in communication with a data structure generation component that provides functionality for generating a data structure for use by the k-mer selection component. In some embodiments, the data structure generation component is an executable application program that generates data structures, such as hash tables. In still even another embodiment, the data structure generation component stores a generated hash table in the storage element 128. In some embodiments, the data structure generation component transmits an identification of a generated data structure 212 to the k-mer selection component 202. In some embodiments, a user provides the k-mer selection component 202 with an identification of a generated data structure 212 in which the k-mer selection component 202 may store identifications of k-mers and related data.

In some embodiments, the data structure 212 includes an index in which each row corresponds to a given key or identifier. In some embodiments, the index is implemented using any data structure, including arrays, tables, hash tables, and linked lists, binary trees, red-black trees, and other trees known to those of ordinary skill in the art. In some embodiments, the index is implemented using any technique for implementing a hash table. For example, in some embodiments, the index is implemented as an array of linked lists, where each linked list corresponds to a row of the index. In some embodiments, the table is implemented as a two dimensional array. In some such embodiments, if a row of the array becomes full, the least recently used location identifier in the row may be discarded. In some embodiments, the index is implemented as an array where hash collisions are resolved by placing location identifiers in array slots subsequent to a slot of the overloaded hash value.

In some embodiments in which the data structure 212 is a hash table, the data structure 212 is a data structure that uses a hash function to map an identifier (also referred to as a key) to associated values; the hash function transforms the key into an index (hash) of an array element storing the corresponding value. In some such embodiments, the hash function is any hash function or checksum algorithm that has sufficiently few collisions for the type of data used. In some embodiments, hash functions include, without limitation, AP Hash, Adler 16, Adler 32, Adler 8, BKDR Hash, BP Hash, CK SUM MPEG-2, CK Sum, CRC DNP, CRC-16, CRC-16 (IBM), CRC-16 (Kermit), CRC-16 (Modbus), CRC-16 (Sick), CRC-16 (X25), CRC-16 CCITT (0x1D0F), CRC-16 CCITT (0xFFFF), CRC-16 CCITT (XModem), CRC-16 CCITT (ZModem), CRC-24, CRC-32, CRC-32 bzip2, CRC-32 jam, CRC-32 mpeg-2, CRC-64, CRC-64 (ECMA), DJB Hash, Dek Hash, Elf, FCS 16, FCS 32, FNV 0 8-1024, FNV 1 8-1024, FNV 1a 8-1024, Fletcher-16, Fletcher-32, Fletcher-8, GHash 3, GHash 5, GOST, Haval 128 (3-5), Haval 160 (3-5), Haval 192 (3-5), Haval 224 (3-5). Haval 256 (3-5), JHash, JS Hash, MD-2, MD-4, MD-5, Murmur, Murmur 2, One at a time, PJW Hash, Pearson Hash, RIPEMD 128, RIPEMD 160, RIPEMD 320, RS Hash, SDBM Hash, Sapphire 128, Sapphire 160, Sapphire 192, Sapphire 224, Sapphire 256, Sapphire 288, Sapphire 320, Sha-1, Sha-224, Sha- 256, Sha-384, Sha-512, Size64, Sum BSD, Sum Sys V, Sum16, Sum24, Sum32, Sum64, Sum8, Tiger 128, Tiger 160, Tiger 192, Whirlpool 512, XOR16, XOR32, XOR8, XUM 32, or a hash function that produces minimal or substantially no collisions for the type of data on which the hash function is applied; or any other hash function able to produce results suitable for the systems and methods described herein.

In some embodiments, the computing device 100 maintains and stores computed hashes based upon a determination as to which data to delete to make room for new data in order to maintain an overall maximum size. In some embodiments, the data structure 212 is purged by using an aging algorithm. In some such embodiments, the aging algorithm may be any page replacement algorithm, such as Least Recently Used (LRU), Not Recently Used (NRU), Active Replacement Cache (ARC), First-in, First-out (FIFO), Least Frequency Usage (LFU), or any similar algorithm that allows the storage element 128 to evict entries on an efficient basis. In some embodiments, such an algorithm increments a counter on a hit and when space is needed on a miss, the entries that have the lowest counter and size that produces the least impact to bandwidth are evicted. Further embodiments can include a caching system where there is persistent caching of high frequency resources on a client, computing machine or remote computing machine's persistent storage disk.

In some embodiments, the k-mer selection component 202 includes an application program executed by the computing device 100 to select k-mers for inclusion in an initial plurality of k-mers 210. In another embodiment, the k-mer selection component 202 accesses at least one filter to select k-mers for inclusion in an initial plurality of k-mers 210. In some embodiments, the k-mer selection component 202 applies the at least one filter to a k-mer in the target set. In yet another embodiment, the k-mer selection component 202 includes functionality for storing, in the data structure 212, an identification of a k-mer in the initial plurality of k-mers, responsive to an application of the at least one filter to the k-mer.

In some embodiments, the k-mer selection component 202 includes functionality for storing, in the data structure 212, an identification of a k-mer. In some embodiments, the k-mer selection component 202 includes functionality for storing, in the data structure 212, an identification of a key in a hash table. In some embodiments, the key is associated with at least one k-mer identified within the data structure 212. In some embodiments, the k-mer selection component 202 includes functionality for storing, in the data structure 212, for each k-mer in the initial plurality of k-mers, an identification of a key associated with each k-mer. In some of these embodiments, the key contains data representative of a nucleotide sequence (or the reverse complement thereof) of a k-mer in the initial plurality of k-mers. In some embodiments, a string comparison is made between a nucleotide sequence of a k-mer and the reverse complement, and the lower value between the two is stored in the data structure. (In some embodiments, the higher value is stored). In some embodiments, the k-mer selection component 202 includes functionality for storing, in the data structure 212, an identification of the target genome from which the initial plurality of k-mers was identified. In some embodiments, the k-mer selection component 202 includes functionality for storing, in the data structure 212, an identification of a position within the target genome of a k-mer in the initial plurality of k-mers (e.g., the first k-mer or the second-kmer). In some embodiments, the k-mer selection component 202 includes functionality for storing, in the data structure 212, an identification of a strand of each k-mer in the initial plurality (i.e., the strand of the target genome from which the k-mer was identified). By way of example, and in further embodiments, the k-mer selection component 202 may include application program code that, when executed by the computing device 100, modifies the data structure 212 to include data comprising an identification of a k-mer or data associated with the k-mer (such as a position within a target genome or a key).

The k-mer analysis component 208 executes on the computing device 100 and identifies the first k-mer and the second k-mer as a primer pair for use in a polymerase chain reaction. In some embodiments, the k-mer analysis component 208 stores an identification of the primer pair on the storage element 128 of the computing device 100. In some embodiments, the k-mer analysis component 208 stores the identification in the data structure 212. In other embodiments, the k-mer analysis component 208 stores the identification in a second data structure 212b. In further embodiments, the k-mer analysis component 208 includes functionality for storing the identification in the data structure 212. In one of these embodiments, and by way of example, the k-mer analysis component 208 may include application program code that, when executed by the computing device 100, modifies a data structure to include data comprising an identification of the primer pair.

In some embodiments, the k-mer analysis component 208 is in communication with a user interface generation component (not shown). In some embodiments, the user interface generation component includes a retrieval component for retrieving the identification of the primer pair from the storage element 128. In some embodiments, the user interface generation component includes a receiver receiving, from the k-mer analysis component 208, an identification of the primer pair. In some of these embodiments, the user interface generation component includes a display component generating a user interface and displaying the retrieved identification to a user of the computing device 100. In some embodiments, the k-mer analysis component 208 includes a user interface generation component.

In some embodiments, the k-mer analysis component 208 is in communication with an alert generation component (not shown). In some embodiments, the alert generation component includes a retrieval component for retrieving the identification of the primer pair from the storage element 128. In some embodiments, the alert generation component includes a receiver receiving, from the k-mer analysis component 208, an identification of the primer pair. In some embodiments, the alert generation component includes a transmitter sending the retrieved identification to a user of the computing device 100; for example, the alert generation component may include or be in communication with a user interface generation component that displays an alert, notification, or other user interface element to a user of the computing device 100, such as a text box via a display device 124. In some embodiments, the alert generation component includes a transmitter sending the retrieved identification to a user of a second computing device 100; for example, the alert generation component may send an electronic message to another computing device. In some embodiments, the k-mer analysis component 208 includes an alert generation component. It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C#, PROLOG, or in any byte code language such as JAVA. The software programs may be stored on or in one or more articles of manufacture as object code. Having described certain embodiments of methods and systems for identifying a pair of primers for polymerase chain reaction specific to one or more target genomes within a target set but not to any non-target genomes within a non-target set, it will now become apparent to one of skill in the art that other embodiments incorporating the concepts of the invention may be used. Therefore, the disclosure should not be limited to certain embodiments, but rather should be limited only by the spirit and scope of the following claims.

EXAMPLES

The following examples describe some exemplary modes of making and practicing the present invention. It should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

Identifying Primer and Probe Sets Specific to Methicillin-Resistant *Staphylococcus aureus* (MRSA) Using Method 1

The present Example demonstrates utility of disclosed methods for identifying PCR primers to distinguish between closely related strains and/or species of pathogenic bacteria. In the present Example, PCR primers to distinguish methicillin-resistant *Staphylococcus aureus* (MRSA) from methicillin-sensitive *S. aureus* (MSSA) and methicillin-resistant coagulase negative *Staphylococcus* (MR-CNS) were identified using "method 1," certain embodiments of the present invention in which primers unique to the target set (as compared to the non-target set) are found. In order to compare results obtained using inventive methods described herein with results obtainable with a method known in the art, we first tested how well Insignia (Phillippy et al. (2007)) could find MRSA-specific probes. Insignia is a software program that finds PCR primers by generating "signatures," regions common to all the members of a target set of genomes, but not present in any members of a non-target set of genomes. Using a target genome set comprising the COL strain as the base strain and nine other MRSA strains (whose genomic sequences were available) and a non-target set comprising all other sequenced bacterial genomes, Insignia was unable to find any signatures.

We then tested 'method 1' using a target set comprising ten strains of MRSA (as shown in Table 2 below) and eight strains in the non-target set. The non-target set comprised methicillin-sensitive *S. aureus* and coagulase negative *Staphylococcus* strains. Method 1 looks for k-mers unique to the target set and then evaluates pairs of such k-mers that can be used as PCR primers. Method 1 was run by calling, in sequential order, scripts pickKmers.pl (depicted in Appendix A), mapKmers.seqmap.pl (depicted in Appendix E), and pickPairs.pl (depicted in Appendix F), with configuration files depicted in Appendices G and H and the uniqueType variable set to 'single'.

TABLE 2

Strains used in target set (MRSA) and non-target set (MSSA, CNS)

| Strain | Refseq ID | Type |
| --- | --- | --- |
| Staphylococcus_aureus_aureus_MRSA252 | NC_002952 | MRSA |
| Staphylococcus_aureus_COL | NC_002951 | MRSA |
| Staphylococcus_aureus_JH1 | NC_009632 | MRSA |
| Staphylococcus_aureus_JH9 | NC_009487 | MRSA |
| Staphylococcus_aureus_Mu3 | NC_009782 | MRSA |
| Staphylococcus_aureus_Mu50 | NC_002758 | MRSA |
| Staphylococcus_aureus_MW2 | NC_003923 | MRSA |
| Staphylococcus_aureus_N315 | NC_002745 | MRSA |
| Staphylococcus_aureus_USA300 | NC_007793 | MRSA |
| Staphylococcus_aureus_USA300_TCH1516 | NC_010079 | MRSA |
| Staphylococcus_aureus_aureus_MSSA476 | NC_002953 | MSSA |
| Staphylococcus_aureus_NCTC_8325 | NC_007795 | MSSA |
| Staphylococcus_aureus_Newman | NC_009641 | MSSA |
| Staphylococcus_aureus_RF122 | NC_007622 | MSSA |
| Staphylococcus_epidermis_ATCC_12228.fa | NC_004461 | MR-CNS |
| Staphylococcus_epidermis_RP62A.fa | NC_002976 | MR-CNS |
| Staphylococcus_haemolyticus.fa | NC_007168 | MR-CNS |
| Staphylococcus_saprophyticus.fa | NC_007350 | MR-CNS |

Method 1 as it was used in this example did not identify a single primer/probe set that was unique to the target set and present in all genomes in the target set. Method 1 identified many primer/probe sets that were unique to the target set and present in some of the genomes in the target set. Therefore, we ran a set-covering algorithm on the primer/probe sets identified by method 1. Table 3 depicts one possible combination of primer/probe sets that together are 1) unique to the target set and 2) cover all members of the target set.

TABLE 3

```
Lists of primers/probes that can distinguish
   a set of MRSA bacteria versus non-MRSA
```

| Genomes Hit | Primer/probe sequences (5'→3') | Size | TM (° C.) |
| --- | --- | --- | --- |
| 1, 3, 4, 5, 6, 9 | Left primer: ATTGTGTCATTCCTCATAGCTCC (SEQ ID NO: 1) Right primer: GGAAGTGAGCGACATGTTAGA (SEQ ID NO: 2) Probe: TGCTATGCGATAAAAGAGATAAACGC CAAACCC (SEQ ID NO: 3) | 256 | 52.36 |
| 2, 5, 6, | Left primer: | 267 | 51.66 |

TABLE 3-continued

Lists of primers/probes that can distinguish
a set of MRSA bacteria versus non-MRSA

| Genomes Hit | Primer/probe sequences (5'→3') | Size | TM (° C.) |
|---|---|---|---|
| 7, 8, 9 | CACCACTCACTGTTCCCTC (SEQ ID NO: 4)<br>Right primer:<br>AAGCAGTCGAAGCTGAACC (SEQ ID NO: 5)<br>Probe:<br>AACTGAAAGTGGTACAATTCACGCGA TTCAC (SEQ ID NO: 6) | | |
| 0, 2, 5, 6 | Left primer:<br>ACCCAACGAAAGAACTAGACA (SEQ ID NO: 7)<br>Right primer:<br>ACCTTGTCGCCATTAACTCA (SEQ ID NO: 8)<br>Probe:<br>CTAACTGGCTCTCCTTTTTGTAACGG TCC (SEQ ID NO: 9) | 90 | 51.03 |

While only one possible combination covering the target set is depicted, many possible combinations of primer/probe sets can be used to distinguish the target set from the non-target set.

Example 2

Identifying Primer and Probe Sets Specific to Methicillin-Resistant *Staphylococcys aureus* (MRSA) Using Method 2

"Method 2" refers to embodiments of the invention in which pairs of PCR primers that are unique to the target set are found. In method 2, it is possible for identified pairs to comprise one or more primers that by themselves are not unique to the target set, but the combination of the primers is unique. We tested method 2 on the same target set and non-target set used in Example 1. Method 2 was run by calling, sequentially, scripts pickKmers.pl (depicted in Appendix A), mapKmers.seqmap.pl (depicted in Appendix E and pickPairs.pl (depicted in Appendix F), using configuration files as depicted in Appendices G and H with the uniqueType variable set to 'combine'. Method 2 as it was run in this Example found primer/probe sets unique to just the MRSA strains. Table 3 lists a sample of these primer/probe sets. The primers were mapped to the COL genome to determine their location. They were found to flank the boundary of the staphylococcal cassette chromosome mec (SCCmec), a region in which MRSA-specific primers had been found by previous methods. (See, e.g., U.S. Pat. No. 6,156,507 and U.S. patent applications US2006/0252078, US2005/0019893, and US2007/0082340) Thus, the present Example demonstrates the validity of inventive methods in finding primers and probes specific to a target set of bacterial genomes, but not to related, non-target genomes. All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls. The section headings used herein are for organizational purposes only and are not to be construed as limiting the subject matter described in any way.

Appendix A

PERL Script pickKmers.pl

```
#!/usr/bin/perl
#This program finds kmers in genomes that can be potential PCR primers and outputs #them
into a text file. Each kmer is listed with the genomes they are found in, the #position, as well
as strand.
use strict;
use lib ".";
use multiSpi; #process configuration
use TM;      #melting temp calculations
use simpleAlign; #self hybridization calculations
##########PROCESSING CONFIGURATION FILES
my $configFile=shift;
my $genomeInfo={ }; #store genome information
my $config={ }; #store input variable
multiSpi::processConfigFile($configFile,$config);
my $kmerLengthMin=$config->{kmerLengthMin};
my $kmerLengthMax=$config->{kmerLengthMax};
##filter parameters
my $maxRunBases=$config->{maxRunBases};
my $localPrimerAlign=$config->{localPrimerAlign};
my $globalPrimerAlign=$config->{globalPrimerAlign};
my $minTm=$config->{minTM};
my $maxTm=$config->{maxTM};
my $minGC=$config->{minGC};
my $maxGC=$config->{maxGC};

my $minGenomesRepresented=$config->{minGenomesRepresented};#for a kmer to be
considered it needs to cover this number of target genomes
my $printTargets=$config->{printTargets}; #this is 1 if the coordinates within target
genomes should be written
my $genomeFiles=$config->{genomeConfig}; #list of fasta files
multiSpi::processGenomeFiles($genomeFiles,$genomeInfo);
mkdir($config->{workDir}) if !(-d ($config->{workDir}));
my $outFile=$config->{workDir}."/".$config->{kmerTargetFile};
```

```perl
my $dir=$genomeInfo->{genomeDir};
my $uniqueType=$config->{uniqueType}||'combined'; #this refers to two methods
described in claims method 1 is the 'single' method. Method 2 is the 'combined' method. A
'singleOld' method was a previous method that gave similar results to the 'single' method.
###########
multiSpi::printVars($config);
my %masterMers; #holds info on all of the mers
my %badMers; #hold kmers that previously failed filter
foreach my $targetNum (0..scalar @{$genomeInfo->{targets}}-1){ #numbering targets from
0 but will be written out as this number +1
    buildKmer($targetNum);
}
open OUT,">$outFile";
printMers( );
exit;
sub buildKmer{
    my ($genomeNum)=@_;
    my %genomeMers;
    my @kmerLengths=($kmerLengthMin..$kmerLengthMax);
    my $file=$dir."/".$genomeInfo->{'targets'}->[$genomeNum];
    print "$genomeNum,$file\n";
    ###load sequence
    open SEQ,$file or die "Can't open $file\n";;
    <SEQ>;
    my $seq;
    while (my $line=<SEQ>) {
       chomp $line;
       $seq.=$line;
    }
    my $length=length($seq); #loop through sequence
    ###Populate genome specific table
    foreach my $pos (0..$length-1) { #loop through position
       print STDERR "$pos\n" if $pos%100000==0;
       foreach my $kmerLength (@kmerLengths) { #loop through kmer size
           next if $pos+$kmerLength>$length;
           my $seq=uc substr($seq,$pos,$kmerLength); #this is the k-mer
           next unless $seq=~/^[ACGTacgt]+$/; #do not want Ns
           my $revSeq=revcom($seq);
           my $cmp=$seq cmp $revSeq; #string comparison
           my $mer=$seq;
           my $strand='+';
           if ($cmp == 1) {        #each kmer has a reverse complement
              $mer=$revSeq; #store the lower valuse of the mer
              $strand='-'; #or reverse complement
           }
           next if exists($badMers{$mer});
           if (exists($masterMers{$mer})){
              $genomeMers{$mer}->[0]++;
              if ($uniqueType eq 'singleOld' ||$printTargets==1){
                 $genomeMers{$mer}->[2]=[$pos,$strand];
              }
              next;
           }
           my $tm=filter($config,$mer); #if a good fileter, return TM. Otherwise return 0
           if ($tm) {
              $tm=sprintf(
"%.3f", $tm);
              $tm=int($tm*1000);
              $genomeMers{$mer}->[0]++;
              $genomeMers{$mer}->[1]=$tm;
              if ($uniqueType eq 'singleOld' ||$printTargets==1 ){
                 $genomeMers{$mer}->[2]=[$pos,$strand];
              }
           } else{
              $badMers{$mer}=1;
           }
       }
    }
    #add to master table
    foreach my $mer (keys %genomeMers){
       if ($genomeMers{$mer}->[0]>1){
         $masterMers{$mer}->[0]=0;
       } elsif (exists ($masterMers{$mer}) && ($masterMers{$mer}->[0]==0)){
         next;
       } elsif (!exists ($masterMers{$mer})) {
          $masterMers{$mer}->[0]=1;
          $masterMers{$mer}->[1]=$genomeMers{$mer}->[1];
          if ($uniqueType eq 'singleOld'||$printTargets==1){
            $masterMers{$mer}->[2]->{$genomeNum}=$genomeMers{$mer}->[2];
          }
```

```perl
    } else {
      $masterMers{$mer}->[0]++;
      if ($uniqueType eq 'singleOld'||$printTargets==1){
        $masterMers{$mer}->[2]->{$genomeNum}=$genomeMers{$mer}->[2];
      }
    }
   }
  }
 }
}
sub revcom{ #reverse complement
 my $seq=shift;
 $seq=reverse($seq);
 $seq=~tr/ACGTacgt/TGCAtgca/;
 return $seq;
}
sub filter{
 my ($config,$seq)=@_;
 my $tm=TM::TM($seq);
 return 0 unless ($tm>=$minTm&&$tm<=$maxTm);
 my $gc=$seq=~tr/GCgc/GCgc/;
 my $gcP=$gc/length($seq);
 return 0 unless ($gcP>$minGC/100 && $gcP<$maxGC/100);
 my $aRun='A'x($maxRunBases+1);
 my $cRun='C'x($maxRunBases+1);
 my $gRun='G'x($maxRunBases+1);
 my $tRun='T'x($maxRunBases+1);
 my $run=$seq=~/($aRun|$cRun|$gRun|$tRun)/;
 return 0 if $run;
 my $seq2=reverse($seq);
 $seq2=~tr/ACGTacgt/TGCAtgca/;
 my ($localScore,$globalScore)=simpleAlign::simpleAlign($seq,$seq2);
 return 0 if $localScore>$localPrimerAlign;
 return 0 if $globalScore>$globalPrimerAlign;
 return $tm;
}
sub printMers{
  foreach my $mer (keys %masterMers){
      my ($count,$tm)=@{$masterMers{$mer}};
      next unless $count>=$minGenomesRepresented;
      my $info;
      if ($uniqueType eq 'singleOld' || $printTargets==1){
        $info="\t";
        foreach my $g (sort {$a<=>$b}keys %{$masterMers{$mer}->[2]}){
          my ($pos,$strand)=@{$masterMers{$mer}->[2]->{$g}};
          my $showG=$g+1;
          $info.="$showG,$pos,$strand;";
        }
      }
      print OUT "$mer\t$tm\t$count$info\n";
  }
}
__END__
```

Appendix B

PERL Module multiSpi.pm

In some embodiments PERL module multiSpi.pm may be used by one or more scripts to parse configuration files.

```perl
package multiSpi;
#file for processing configuration files
use strict;
use XML::Simple;
sub processGenomeFiles{
    my ($genomeFiles,$genomeInfo)=@_;
    my $xml = new XML::Simple;
    my $data = $xml->XMLin($genomeFiles);
    my @targets=split /\n/,$data->{TARGETS};
    for (my $c=scalar @targets-1;$c>=0;$c--){
      splice (@targets,$c,1) if (!$targets[$c]);
      splice (@targets,$c,1) if ($targets[$c]=~/^\#/);
    }
    $genomeInfo->{targets}=\@targets;
    my @related=split /\n/,$data->{RELATED};
    for (my $c=scalar @related-1;$c>=0;$c--){
      splice (@related,$c,1) if (!$related[$c]);
      splice (@related,$c,1) if ($related[$c]=~/^\#/);
    }
    $genomeInfo->{related}=\@related;
    $genomeInfo->{genomeDir}=$data->{GENOMEDIR};
    $genomeInfo->{genomeDir}=~s/\s//g;
}
sub processConfigFile{
 my ($configFile,$config)=@_;
 open FILE,$configFile or die "Can not open $configFile\n";;
 my $primer3Vals=0;
 while (my $line=<FILE>){
    next if $line=~/^\#/;
    chomp $line;
    if ($line=~/<PRIMER3>/){
      $primer3Vals=1 ;
      next;
    }
    my ($var,$val)=split /=/,$line;
    if ($primer3Vals){
      $config->{PRIMER3}->{$var}=$val;
    } else{
```

-continued

```
        $config->{$var}=$val;
    }
}
my $kmerLengths=$config->{kmerlengths};
my @kmerLengths;
if ($kmerLengths=~/(\d+)\.\.(\d+)/){
    foreach my $c ($1..$2){
        push @kmerLengths,$c;
    }
}elsif ($kmerLengths=~/,/){
    @kmerLengths=split /,/,$kmerLengths;
}
$config->{kmerLengths}=\@kmerLengths;
}
1;
sub printVars{
    my $config=shift;
    foreach my $var (sort keys %{$config}){
        my $val=$config->{$var};
        print "$var\t$val\n";
    }
}
```

Appendix C

PERL Module TM.pm

In some embodiments PERL module TM.pm may be used to find the melting temperature of primers.

```
package TM;
my %thermo_values = ('AA' => {'enthalpy' => -7.9,
                              'entropy' => -22.2},
                     'AC' => {'enthalpy' => -8.4,
                              'entropy' => -22.4},
                     'AG' => {'enthalpy' => -7.8,
                              'entropy' => -21},
                     'AT' => {'enthalpy' => -7.2,
                              'entropy' => -20.4},
                     'CA' => {'enthalpy' => -8.5,
                              'entropy' => -22.7},
                     'CC' => {'enthalpy' => -8,
                              'entropy' => -19.9},
                     'CG' => {'enthalpy' => -10.6,
                              'entropy' => -27.2},
                     'CT' => {'enthalpy' => -7.8,
                              'entropy' => -21},
                     'GA' => {'enthalpy' => -8.2,
                              'entropy' => -22.2},
                     'GC' => {'enthalpy' => -9.8,
                              'entropy' => -24.4},
                     'GG' => {'enthalpy' => -8,
                              'entropy' => -19.9},
                     'GT' => {'enthalpy' => -8.4,
                              'entropy' => -22.4},
                     'TA' => {'enthalpy' => -7.2,
                              'entropy' => -21.3},
                     'TC' => {'enthalpy' => -8.2,
                              'entropy' => -22.2},
                     TG => {'enthalpy' => -8.5,
                              'entropy' => -22.7},
                     'TT' => {'enthalpy' => -7.9,
                              'entropy' => -22.2},
                     'A' => {'enthalpy' => 2.3,
                              'entropy' => 4.1},
                     'C' => {'enthalpy' => 0.1,
                              'entropy' => -2.8},
                     'G' => {'enthalpy' => 0.1,
                              'entropy' => -2.8},
                     'T' => {'enthalpy' => 2.3,
                              'entropy' => 4.1}
                    );
sub TM {
    my ($seq, %args) = @_;
    my $saltConc = 0.05; #default salt concentration (molar units)
    my $oligoConc = 0.000000050; # default oligo concentration
    (molar units)
    if ($args{'-salt'}) { $saltConc = $args{'-salt'}}; #salt concentrations
    if ($args{'-olgio'}) {$oligoConc=$args{'oligo'}};
    my $length = length($seq);
    my $sequence = uc $seq;
    my @dinucleotides;
    my $enthalpy;
    my $entropy;
    while ($sequence =~ /(.)(?=(.))/g) {
        push @dinucleotides, $1.$2;
    }
    for (@dinucleotides) {
        $enthalpy += $thermo_values{$_}{enthalpy};
        $entropy += $thermo_values{$_}{entropy};
    }
    $enthalpy += $thermo_values{substr($sequence, 0, 1)}{enthalpy};
    $entropy += $thermo_values{substr($sequence, 0, 1)}{entropy};
    $enthalpy += $thermo_values{substr($sequence, -1, 1)}{enthalpy};
    $entropy += $thermo_values{substr($sequence, -1, 1)}{entropy};
    my $delta_S=$entropy;
    my $delta_H=$enthalpy*1000;
    $entropy -= 1.4;
    my $r = 1.987; #molar gas constant
    $delta_S = $delta_S + 0.368 * (length($sequence) -1) *
    log($saltConc);
    my $Tm = $delta_H / ($delta_S + 1.987 * log($oligoConc/4)) -
    273.15;
    return $Tm;
}
1;
```

Appendix D

PERL Module simpleAlign.pm

In some embodiments the PERL module simpleAlign.pm may be used by one or more scripts to generate an ungapped global and local alignment score.

```
package simpleAlign;
use strict;
#performs a simple ungapped alignment
sub simpleAlign{
    my ($seq1,$seq2)=@_;
    my $length1=length($seq1);
    my $length2=length($seq2);
    my @seq1=split //,$seq1;
    my @seq2;
    $seq2[$length1-1]=undef;
    splice(@seq2,$length1-1,1,split //,$seq2);
    my $maxLocalScore=0;
    my $maxGlobalScore=0;
    while (@seq2){
        my $curScore;
        for (my $c=0; $c<$length1;$c+=1){
            next unless defined($seq2[$c]);
            if ($seq1[$c] eq $seq2[$c]){
                $curScore+=1;
            } else {
                $curScore-=1;
            }
            $maxLocalScore=$curScore if $curScore>$maxLocalScore;
            $maxLocalScore=0 if $maxLocalScore<0;
        }
        $maxGlobalScore=$curScore if $curScore>$maxGlobalScore;
        shift @seq2;
    }
    return ($maxLocalScore,$maxGlobalScore);
}
1;
```

Appendix E

PERL Script mapKmers.seqmap.pl

```perl
#!/usr/bin/perl
# program will take kmers from pickKmers.pl and match them to related
genomes using seqmap
use strict;
use lib ".";
use multiSpi;
use Cwd;
##########PROCESSING CONFIGURATION FILES
my $configFile=shift;#"/home/projects/genomics/data/SPI/configs/
swine.cu.txt";
my $config={ };
multiSpi::processConfigFile($configFile,$config);
my $genomeFiles=$config->{genomeConfig};
my $genomeInfo={ };
my $misMatchCutoff=$config->{misMatchCutoff};
my $workDir=$config->{workDir};
my $kmerTargetFile=$config->{kmerTargetFile};
my $kmerTargetPlusRelatedFile=$config->{kmerTargetPlusRelatedFile};
my $seqmapBin=$config->{seqmapBin};
my $seqmapParms=$config->{seqmapParms};
my $seqmapMM=$config->{seqmapMM};
my $inFile="$workDir/$kmerTargetFile";
my $outFile="$workDir/$kmerTargetPlusRelatedFile";
my $maxAllowableRelatedRepeats=$config-
>{maxAllowableRelatedRepeats}||10;
multiSpi::processGenomeFiles($genomeFiles,$genomeInfo);
my $genomeDir=$genomeInfo->{genomeDir};
my @relatedGenomes=@{$genomeInfo->{related}};
multiSpi::printVars($config);
###############
#### edit this for each machine
my $tmp="/scratch/lance";
if (! (-w $tmp)){
    $tmp="/tmp/";
}
##########
my %mers;
my $counter;
my %genomeNums;
my $counter=-1;
#for non-target genomes, genomes counted from -1 down
foreach my $genomeFile (@relatedGenomes){
    open IN, "$genomeDir/$genomeFile";
    while (my $line=<IN>){
        next unless $line=~/>(\S+)/;
        $genomeNums{$1}=$counter--;
    }
}
#print sets of kmers
my $tmpKmers="$tmp/$$.tmpKmers.txt";
my $kmerCounter=0;
open KMERS,$inFile or die "Can't open $inFile\n";;
while (my $line=<KMERS>){
    if (($kmerCounter%5000000)==0){ #limit number of kmers mapped
    at a time
        close TMPKMERS;
        if ($kmerCounter){
            mapKmers( );
        }
        open TMPKMERS,">$tmpKmers";
    }
    my ($kmer)=split /\t/,$line;
    print TMPKMERS ">$kmer\n$kmer\n";
    $kmerCounter++;
}
close TMPKMERS;
mapKmers( );
unlink $tmpKmers;
printKmers( );
exit;
##using seqmap to map kmers to non-target genome
sub mapKmers{
    foreach my $g (0..scalar @relatedGenomes-1) {
        my $genome=$relatedGenomes[$g];
        my $file="$genomeDir/$genome";
        `cp $file $tmp/$$.genome.tmp`;
        my $seqMaqpOut="$tmp/$$.seqmap.out";
        `$seqmapBin $seqmapMM $tmpKmers $tmp/$$.genome.tmp
$tmp/$$.seqmap.out $seqmapParms`;
        open RESULTS,"$tmp/$$.seqmap.out";
        while (my $line=<RESULTS>) {
            chomp $line;
            my ($target,$coord,$tSeq,$probeId,$probeSeq,$mm,$strand)=split
/\t/,$line;
            my ($id)=$target=~/^(\S+)/;
            my $genomeNum=$genomeNums{$id};
            next unless defined $genomeNum;
            $mers{$probeSeq}->{$genomeNum}->{$coord}=[$strand,$mm];
        }
    }
}
#go through kmer files and print kmer and matches to non targets
sub printKmers{
    open KMERS,$inFile;
    open OUT,">$outFile";
    while (my $line=<KMERS>) {
        chomp $line;
        my ($mer,$tm,$count,$targets)=split /\t/,$line;
        next unless $mer;
        my ($kmer)=$line=~/^(\S+)\s/;
        next if (exists($mers{$mer})&&$mers{$mer}==0);
        my $repeatCount;
        foreach my $g (reverse sort {$a<=>$b}keys %{$mers{$mer}}) {
            my $gCount=scalar keys %{$mers{$mer}->{$g}};
            $repeatCount='rep' if $gCount>$maxAllowableRelatedRepeats;
        }
        next if $repeatCount;
        print OUT "$kmer\t$tm\t$targets";
        foreach my $g (reverse sort {$a<=>$b}keys %{$mers{$mer}}) {
            foreach my $pos (sort {$a<=>$b} keys %{$mers{$mer}->{$g}}) {
                my ($dir,$misMatch)=@{$mers{$mer}->{$g}->{$pos}};
                print OUT "$g,$pos,$dir,$misMatch;";
            }
        }
        print OUT "\n";
    }
}
_END_
```

Appendix G

Configuration File config.txt

```
kmerLengthMin=18
kmerLengthMax=26
minTM=51
maxTM=53
minGC=30
maxGC=80
maxRunBases=4
localPrimerAlign=7
globalPrimerAlign=2
workDir=results
kmerTargetFile=test.primers.txt
kmerTargetPlusRelatedFile=test.primersPlus.txt
primerPairsOligoFile=test.primer.pairsOligo.txt
genomeConfig=genomeFiles.txt
maxProductSize=300
minGenomesRepresented=3
misMatchCutoff=3
minInternalLength=30
maxPairsPerKmer=10
maxPairs2Check=20
genomeCoverageTotal=100
minOligoTM=8
maxOligoTM=10
oligoBuffer=5
```

-continued

```
primerTMDif=2
#/home/palmla00/programs/seqmap
seqmapBin=./seqmap
seqmapParms= /output_all_matches
seqmapMM=3
pairFile=test.primerPairs.txt
uniqueType=combined
<PRIMER3>
PRIMER_INTERNAL_OLIGO_MIN_GC=25
PRIMER_INTERNAL_OLIG_MAX_GC=75
PRIMER_TASK=pick_pcr_primers_and_hyb_probe
PRIMER_TM_SANTALUCIA=1
PRIMER_SALT_CORRECTIONS=1
PRIMER_PICK_ANYWAY=1
PRIMER_EXPLAIN_FLAG=1
PRIMER_WT_COMP_ANY=1
PRIMER_WT_COMP_END=1
PRIMER_PAIR_WT_COMPL_ANY=2
PRIMER_PAIR_WT_COMPL_END=2
PRIMER_WT_COMPL_ANY=2
PRIMER_WT_COMPL_END=2
PRIMER_PAIR_WT_COMPL_ANY=2
PRIMER_PAIR_WT_COMPL_END=2
PRIMER_FILE_FLAG=1
PRIMER_INTERNAL_OLIGO_SELF_ANY=10
PRIMER_INTERNAL_OLIGO_SELF_END=10
PRIMER_INTERNAL_OLIGO_OPT_SIZE=29
PRIMER_INTERNAL_OLIGO_MIN_SIZE=24
PRIMER_INTERNAL_OLIGO_MAX_SIZE=34
PRIMER_INTERNAL_OLIGO_OPT_GC_PERCENT=50
PRIMER_IO_WT_COMPL_ANY=2
PRIMER_IO_WT_COMPL_END=2
PRIMER_NUM_RETURN=5
```

Appendix H

Configuration File genomeFiles.txt

```
<DATA>
<GENOMEDIR>
/home/projects/genomics/data/SPI/genomes/fasta/
</GENOMEDIR>
<TARGETS>
Staphylococcus_aureus_COL.fa
Staphylococcus_aureus_MW2.fa
Staphylococcus_aureus_aureus_MRSA252.fa
Staphylococcus_aureus_USA300.fa
Staphylococcus_aureus_USA300_TCH1516.fa
Staphylococcus_aureus_JH1.fa
Staphylococcus_aureus_JH9.fa
Staphylococcus_aureus_Mu3.fa
Staphylococcus_aureus_Mu50.fa
Staphylococcus_aureus_N315.fa
</TARGETS>
<RELATED>
Staphylococcus_aureus_Newman.fa
Staphylococcus_aureus_RF122.fa
Staphylococcus_epidermidis_ATCC_12228.fa
Staphylococcus_epidermidis_RP62A.fa
Staphylococcus_haemolyticus.fa
Staphylococcus_saprophyticus.fa
Staphylococcus_aureus_aureus_MSSA476.fa
Staphylococcus_aureus_NCTC_8325.fa
</RELATED>
</DATA>
```

---

What is claimed is:

1. A method comprising:
   storing, by a processor of a computing device, an identification of a plurality of k-mers in a target set, wherein
      each respective k-mer of the plurality of k-mers is an oligonucleotide within a particular size range, and
      each respective k-mer of the plurality of k-mers is identified from one or more target genomes in the target set;
   identifying, by the processor, for a first k-mer of the plurality of k-mers, a second k-mer of the plurality of k-mers, wherein the second k-mer is located within a specified number of bases downstream of the first k-mer within at least one of the one or more target genomes in the target set;
   determining, by the processor, that a k-mer pair comprising the first k-mer and the second k-mer fails to recognize each of one or more non-target genomes of a non-target set,
      wherein determining that the k-mer pair fails to recognize a respective non-target genome of the one or more non-target genomes comprises performing operations of:
         (a) attempting to locate the first k-mer within the respective non-target genome of the one or more non-target genomes, wherein, if the first k-mer is not located, the k-mer pair is considered to fail to recognize the respective non-target genome of the one or more non-target genomes,
         (b) responsive to locating the first k-mer within the respective non-target genome of the one or more non-target genomes, attempting to locate the second k-mer within the respective non-target genome of the one or more non-target genomes wherein, if the second k-mer is not located, the k-mer pair is considered to fail to recognize the respective non-target genome of the one or more non-target genomes, and
         (c) responsive to locating the second k-mer within the respective non-target genome of the one or more non-target genomes,
            identifying a number of bases between the first k-mer and the second k-mer within the respective non-target genome of the one or more non-target genomes, and
            comparing the number of bases to the specified number of bases, wherein
               if the number of bases is greater than the specified number of bases, the k-mer pair is considered to fail to recognize the respective non-target genome of the one or more non-target genomes; and
   after determining that the k-mer pair fails to recognize each of the one or more non-target genomes of the non-target set, identifying, by the processor, the k-mer pair as a primer pair for use in a polymerase chain reaction.

2. The method of claim 1, further comprising:
   storing, by the processor, for each respective target genome of the one or more target genomes, an identification of a respective location within the respective target genome of each respective k-mer of the initial plurality of k-mers.

3. The method of claim 2, further comprising sorting, by the processor, for each of the one or more target genomes, the respective location of each respective k-mer of the plurality of k-mers.

4. The method of claim 1, further comprising providing, to a user via a display device in communication with the computing device, an identification of the k-mer pair.

5. The method of claim 1, further comprising:
   applying, by the processor, one or more filters to each respective k-mer of an initial plurality of k-mers, wherein
      a respective k-mer of the initial plurality of k-mers is added as a respective k-mer of the plurality of k-mers dependent upon passing the one or more filters.

6. The method of claim 5, further comprising:
   prior to applying the one or more filters, selecting, by the processor, the one or more filters,
      wherein the one or more filters are configured to filter based on criterion selected from the group consisting of melting temperature, guanine-cytosine content, consecutive runs of the same base, prediction to self-anneal, and combinations thereof.

7. The method of claim 6, wherein:
   selecting the one or more filters comprises selecting at least one filter of the one or more filters based on criterion comprising the melting temperature; and
   passing the at least one filter comprises having a particular melting temperature within a particular range.

8. The method of claim 7, wherein the particular range is from 50 degrees Celsius to 65 degrees Celsius.

9. The method of claim 6, wherein;
   selecting the one or more filters comprises selecting at least one filter of the one or more filters based on criterion comprising the guanine-cytosine content; and
   passing the at least one filter of the one or more filters comprises having a particular guanine-cytosine content within a specified range.

10. The method of claim 9, wherein the specified range is from 20% to 80%.

11. The method of claim 6, wherein:
    selecting the one or more filters comprises selecting at least one filter of the one or more filters based on criterion comprising consecutive runs of the same base; and
    passing the at least one filter comprises lacking consecutive runs of a threshold number of a particular base.

12. The method of claim 11, wherein the threshold number is five.

13. The method of claim 6, wherein:
    selecting the one or more filters comprises selecting at least one filter of the one or more filters based on criterion comprising prediction to self-anneal; and
    passing the at least one filter of the one or more filters comprises not being predicted to self-anneal.

14. The method of claim 1, wherein the specified number of bases is 5000.

15. The method of claim 14, wherein the specified number of bases comprises a range from 100 bases to 400 bases.

16. The method of claim 15, wherein the specified number of bases comprises a range from 100 bases to 300 bases.

17. The method of claim 1, further comprising, prior to identifying the k-mer pair as a primer pair, determining, by the processor, that the first k-mer and the second k-mer do not hybridize to each other.

18. The method of claim 1, wherein identifying the second k-mer of the plurality of k-mers further comprises identifying each of the one or more target genomes of the target set containing the second k-mer within the specified number of bases of the first k-mer, the method further comprising:
    recording a total number of target genomes matched by the k-mer pair.

19. The method of claim 18, further comprising:
identifying, by the processor, for one or more additional pairs of k-mers of the plurality of k-mers, each of the one or more target genomes matched by the respective additional pair of k-mers of the plurality of k-mers, wherein each of the one or more additional pairs of k-mers comprises a respective downstream k-mer of the respective pair of k-mers located within the specified number of bases downstream of a respective upstream k-mer of the respective pair of k-mers;
recording a respective total number of target genomes matched by each respective pair of k-mers; and
sorting the one or more additional pairs of k-mers and the k-mer pair by the respective total number of target genomes matched by each respective pair of k-mers.

20. The method of claim 1, further comprising identifying, by the processor, an oligonucleotide probe that hybridizes to a sequence flanked by the first k-mer and the second k-mer.

21. The method of claim 1, wherein each respective k-mer of the plurality of k-mers is an oligonucleotide between 18 and 28 nucleotides in length, inclusive.

22. A system comprising:
a processor; and
a memory, wherein the memory stores instructions that, when executed by the processor, cause the processor to:
store, in a second memory, a respective identification of each respective k-mer of a plurality of k-mers in a target set, wherein
each respective k-mer of the plurality of k-mers is an oligonucleotide within a particular size range, and
each respective k-mer of the plurality of k-mers is identified from one or more target genomes in the target set;
identify, for a first k-mer of the plurality of k-mers, a second k-mer of the plurality of k-mers, wherein the second k-mer is located within a specified number of bases downstream of the first k-mer within at least one of the one or more target genomes in the target set;
determine that a k-mer pair comprising the first k-mer and the second k-mer fails to recognize each of one or more non-target genomes of a non-target set,
wherein determining that the k-mer pair fails to recognize a respective non-target genome of the one or more non-target genomes comprises performing operations of:
(a) attempting to locate the first k-mer within the respective non-target genome of the one or more non-target genomes, wherein, if the first k-mer is not located, the k-mer pair is considered to fail to recognize the respective non-target genome of the one or more non-target genomes,
(b) responsive to locating the first k-mer within the respective non-target genome of the one or more non-target genomes, attempting to locate the second k-mer within the respective non-target genome of the one or more non-target genomes wherein, if the second k-mer is not located, the k-mer pair is considered to fail to recognize the respective non-target genome of the one or more non-target genomes, and
(c) responsive to locating the second k-mer within the respective non-target genome of the one or more non-target genomes,
identifying a number of bases between the first k-mer and the second k-mer within the respective non-target genome of the one or more non-target genomes, and
comparing the number of bases to the specified number of bases, wherein
if the number of bases is greater than the specified number of bases, the k-mer pair is considered to fail to recognize the respective non-target genome of the one or more non-target genomes;
after determining that the k-mer pair fails to recognize each of the one or more non-target genomes of the non-target set, identify the k-mer pair as a primer pair for use in a polymerase chain reaction; and
store an identification of the primer pair in the second memory.

23. The system of claim 22, wherein the second memory is the memory.

24. The system of claim 22, wherein the instructions further cause the processor to retrieve the identification of the primer pair from the second memory and display the retrieved identification on a display device.

25. The system of claim 22, wherein the instructions further cause the processor to retrieve the identification of the primer pair from the second memory and provide the retrieved identification to a remote computing device.

26. The system of claim 22, wherein the instructions further cause the processor to apply at least one filter to at least one k-mer of an initial plurality of k-mers.

27. The system of claim 26, wherein the instructions further cause the processor to add the at least one k-mer of an initial plurality of k-mers to the plurality of k-mers based in part upon the at least one k-mer passing the filter.

28. The system of claim 22, wherein the instructions further cause the processor to generate a data structure comprising a hash table, wherein the data structure comprises the respective identifications of each respective k-mer of the plurality of k-mers.

29. The system of claim 22, wherein the instructions further cause the processor to store, for each respective k-mer of the plurality of k-mers, a respective identification of a respective key.

30. The system of claim 29, wherein the respective key comprises a hash table key.

31. The system of claim 29, wherein the respective key comprises a nucleotide sequence of the respective k-mer of the plurality of k-mers.

32. The system of claim 22, wherein the instructions further cause the processor to store an identification of the target genome.

33. The system of claim 22, wherein the instructions further cause the processor to store, for each respective k-mer of the plurality of k-mers, a respective identification of a respective position within the target genome.

34. The system of claim 22, wherein the instructions further cause the processor to store, for each respective k-mer of the plurality of k-mers, a respective identification of a respective strand of the target genome from which the respective k-mer of the plurality of k-mers was identified.

35. The system of claim 22, wherein each respective k-mer of the plurality of k-mers is an oligonucleotide of a size between 18 and 28 nucleotide bases, inclusive.

36. A non-transitory computer readable medium, wherein the computer readable medium stores instructions that, when executed by a processor, cause the processor to:
store, in a second memory, a respective identification of each respective k-mer of a plurality of k-mers in a target set, wherein
each respective k-mer of the plurality of k-mers is an oligonucleotide within a particular size range, and each respective k-mer of the plurality of k-mers is identified from one or more target genomes in the target set;

identify, for a first k-mer of the plurality of k-mers, a second k-mer of the plurality of k-mers, wherein the second k-mer is located within a specified number of bases downstream of the first k-mer within at least one of the one or more target genomes in the target set;

determine that a k-mer pair comprising the first k-mer and the second k-mer fails to recognize each of one or more non-target genomes of a non-target set, wherein determining that the k-mer pair fails to recognize a respective non-target genome of the one or more non-target genomes comprises performing operations of:
  (a) attempting to locate the first k-mer within the respective non-target genome of the one or more non-target genomes, wherein, if the first k-mer is not located, the k-mer pair is considered to fail to recognize the respective non-target genome of the one or more non-target genomes,
  (b) responsive to locating the first k-mer within the respective non-target genome of the one or more non-target genomes, attempting to locate the second k-mer within the respective non-target genome of the one or more non-target genomes wherein, if the second k-mer is not located, the k-mer pair is considered to fail to recognize the respective non-target genome of the one or more non-target genomes, and
  (c) responsive to locating the second k-mer within the respective non-target genome of the one or more non-target genomes,
    identifying a number of bases between the first k-mer and the second-k-mer within the respective non-target genome of the one or more non-target genomes, and
    comparing the number of bases to the specified number of bases, wherein
    if the number of bases is greater than the specified number of bases, the k-mer pair is considered to fail to recognize the respective non-target genome of the one or more non-target genomes;

after determining that the k-mer pair fails to recognize each of the one or more non-target genomes of the non-target set, identify the k-mer pair as a primer pair for use in a polymerase chain reaction; and store an identification of the primer pair in the second memory.

\* \* \* \* \*